United States Patent
Dadachova et al.

(10) Patent No.: US 8,652,827 B2
(45) Date of Patent: Feb. 18, 2014

(54) RADIOSYNTHESIS AS AN ALTERNATIVE ENERGY UTILIZATION PROCESS IN MELANIZED ORGANISMS AND USES THEREOF

(75) Inventors: Ekaterina Dadachova, Mahopac, NY (US); Ruth Bryan, New Rochelle, NY (US); Arturo Casadevall, New Rochelle, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 1058 days.

(21) Appl. No.: 12/225,990

(22) PCT Filed: Apr. 2, 2007

(86) PCT No.: PCT/US2007/008292
§ 371 (c)(1),
(2), (4) Date: Aug. 18, 2009

(87) PCT Pub. No.: WO2007/117453
PCT Pub. Date: Oct. 18, 2007

(65) Prior Publication Data
US 2009/0328258 A1 Dec. 31, 2009

Related U.S. Application Data

(60) Provisional application No. 60/789,751, filed on Apr. 5, 2006, provisional application No. 60/819,856, filed on Jul. 10, 2006.

(51) Int. Cl.
*C12N 1/14* (2006.01)
(52) U.S. Cl.
USPC .................................... 435/254.1; 435/252.1

(58) Field of Classification Search
None
See application file for complete search history.

(56) References Cited

U.S. PATENT DOCUMENTS

| | | | |
|---|---|---|---|
| 6,509,325 B1 | 1/2003 | Nosanchuk et al. |
| 7,402,385 B2 | 7/2008 | Dadachova et al. |
| 7,651,689 B2 | 1/2010 | Dadachova et al. |
| 7,709,613 B2 | 5/2010 | Dadachova |
| 2004/0115203 A1 | 6/2004 | Dadachova et al. |
| 2004/0156780 A1 | 8/2004 | Dadachova et al. |
| 2005/0230347 A1 | 10/2005 | Gallas et al. |
| 2006/0018827 A1 | 1/2006 | Dadachova et al. |
| 2006/0039858 A1 | 2/2006 | Dadachova et al. |
| 2007/0237829 A1 | 10/2007 | Dadachova et al. |
| 2008/0226548 A1 | 9/2008 | Dadachova et al. |
| 2011/0300067 A1 | 12/2011 | Dadachova et al. |
| 2012/0003148 A1 | 1/2012 | Dadachova et al. |

OTHER PUBLICATIONS

Williamson et al., Melanin Biosynthesis in *Cryptococcus neoformans*, 1998, J. Bacteriol. 180(6): 1570-1572.*
Sarna et al., Interaction of radicals from water radiolysis with melanin, 1986, Biochimica et Biophysica Acta (BBA)—General Subjects 883(1): 162-167.*

(Continued)

*Primary Examiner* — Jon P Weber
*Assistant Examiner* — Robert Yamasaki
(74) *Attorney, Agent, or Firm* — Amster, Rothstein & Ebenstein LLP

(57) ABSTRACT

This present invention provides methods of enhancing the growth of a microorganism or plant by increasing its melanin content and exposing it to radiation, and methods of using melanized microorganisms to contain or exclude radiation.

9 Claims, 25 Drawing Sheets

(56) References Cited

OTHER PUBLICATIONS

Salas et al., Effect of the laccase gene CNLAC1, on virulence of *Cryptococcus neoformans*, 1996, J. Exp. Med. 184: 377-386.*

Zhdanova et al., Ionizing radiation attracts soil fungi, 2004, Mycological Research 108(9): 1089-1096.*

PCT Notification Concerning Transmittal of International Preliminary Report on Patentability and Written Opinion of the International Searching Authority dated Oct. 30, 2008 in connection with PCT International Patent Application No. PCT/US2007/008292, 8 pages.

Wang Y et al., entitled "Decreased Susceptibility of Melanized *Cryptococcus neoformans* to UV Light," Applied and Environmental Microbiology, Oct. 1994, vol. 60, No. 10, pp. 3864-3866.

Doss R P et al., entitled "Melanin in the extracellular matrix of germlings of *Botrytis cinerea*," Phytochemistry, Jul. 2003, vol. 63, No. 6, pp. 687-691.

Takeuchi S et al., entitled "Melanin acts as potent UVB photosensitizer to cause an atypical mode of cell death in murine skin," PNAS, Oct. 19, 2004, 101(42), pp. 15076-15081.

Karpenko Y V et al., entitled "Comparative responses of microscopic fungi to ionizing radiation and light," Folia Microbiologica, 2006, vol. 51, No. 1, pp. 45-49, Abstract Only.

Blazheevskaia I V, entitled Growth characteristics of microscopic fungi capable of growing actively under the conditions of the 4th unit of the Chernobyl Nuclear Power Plant, Microbiol. Z., May-Jun. 2003, vol. 65, No. 3, pp. 29-38, Abstract Only.

Pulatova M K et al., entitled "Fungal infection of human organs by resistant melanin-synthesizing species is one of the pathogenic factors and one of the real consequences of the accident at Chernobyl power plant," Radiation Biology and Radioecolgy and Radioecology?Russ. Acad. of Sci., Jul.-Aug. 1997, vol. 37, No. 4, pp. 649-656, Abstract Only.

Howell R C et al., entitled "Chemosorption of radiometals of interest to nuclear medicine by synthetic melanins," Nucl Med Biol., Apr. 2008; 35(3):353-357.

Dadachova E et al., entitled "Ionizing Radiation Changes the Electronic Properties of Melanin and Enhances the Growth of Melanized Fungi," PLOS One, 2007, Issue 5, e457, pp. 1-13.

* cited by examiner

A)

B)

A)

B)

A)

B)

C)

D)

A)

B)

C)

D)

C)

D)

E)

A)

B)

C)

D)

C) *H. capsulatum*

D) *C. neoformans*

E) W. dermatitidis isolate 8656

Gauss

F) *C. neoformans* after irradiation

Gauss

A)

B)

C)

D)

A)

B)

RADIOSYNTHESIS AS AN ALTERNATIVE ENERGY UTILIZATION PROCESS IN MELANIZED ORGANISMS AND USES THEREOF

CROSS-REFERENCE TO RELATED APPLICATION

This application is a U.S. national stage entry under 35 U.S.C. §371 of PCT International Patent Application No. PCT/US2007/008292, filed Apr. 2, 2007, and claims priority of U.S. Provisional Patent Application No. 60/789,751, filed Apr. 5, 2006, and of U.S. Provisional Patent Application No. 60/819,856, filed Jul. 10, 2006, the contents of which are hereby incorporated by reference into the subject application.

STATEMENT OF GOVERNMENT SUPPORT

This invention was made with government support under grant number AI52733 awarded by the National Institutes of Health (NIH). The government has certain rights in the invention.

FIELD OF THE INVENTION

The present invention relates to methods of increasing the growth of an organism by increasing its melanin content and exposing the melanized organism to radiation. The invention also provides methods of using melanized microorganisms and melanin to contain or exclude radiation, for example after radiation spills.

BACKGROUND OF THE INVENTION

Throughout this application various publications are referred to in brackets. Citations for these references may be found at the end of the specification immediately preceding the claims. The disclosures of these publications are hereby incorporated by reference in their entireties into the subject application to more fully describe the art to which the subject application pertains.

The term "melanin" originates from a Greek word for black "melanos." Melanin is a high molecular weight pigment, ubiquitous in nature, with a variety of biological functions [1]. Melanins are found in all biological kingdoms. These pigments are among the most stable, insoluble, and resistant of biological materials [2]. Melanins can have different structures depending on the biosynthetic pathway and precursor molecules. Some definitions of melanin have focused on chemical and physical properties of melanins instead of defined structures [46]. Melanins can be synthesized in the laboratory by chemical means or by many living organisms. Melanins formed by the oxidative polymerization of phenolic compounds are usually dark brown or black [2]. However, melanins may have other colors as illustrated by the finding that dopamine-derived melanin is reddish-brown. Fungi can make melanins from at least two major biosynthetic pathways, employing the precursor 1,8-dihydroxynapthalene (DHN melanin) or the oxidation of suitable tyrosine derivatives like dihydroxyphenylalanine (DOPA-melanin) [2]. The fungus C. neoformans can make melanins from a wide variety of phenolic compounds which are oxidized by a laccase enzyme [47-49].

Many fungi constitutively synthesize melanin [2], which is likely to confer a survival advantage in the environment [3] by protecting against UV and solar radiation [reviewed in 4]. Melanized microorganisms inhabit some remarkably extreme environments including highland, Arctic and Antarctic regions [5]. Most dramatically, melanized fungal species colonize the walls in the high constant radiation field of the damaged reactor at Chernobyl [6] as well as the soils around the damaged reactor [7]. These findings and laboratory observations of the resistance of melanized fungi to ionizing radiation [8,9] suggest a role for this pigment in radioresistance.

Despite the presence of melanotic microorganisms in radioactive environments it is unlikely that melanin is synthesized solely for the purposes of protection (shielding) from ionizing radiation. For example, in high elevation regions inhabited by melanotic fungi the background radiations levels are approximately 500-1,000 higher than at sea level, which amounts to a dose of 0.50-1.0 Gy/year. Since the overwhelming majority of fungi, melanized or not, can withstand doses up to $1.7 \times 10^4$ Gy [9], there is no apparent requirement for melanin as a protector. On the other hand, biological pigments play a major role in photosynthesis by converting the energy of light into chemical energy. Chlorophylls and carotenoids absorb light of certain wavelengths and help convert photonic energy into chemical energy during photosynthesis.

Given that melanins can absorb visible and UV light of all wavelengths [10], the inventors hypothesized that melanized microorganisms could use this pigment to scatter/absorb ionizing radiation, a phenomenon that could protect the cell from excessive radiation and also capture energy for a biosynthetic process analogous to photosynthesis. In this scenario, melanin pigment would serve as a transducer of ionizing radiation energy into chemical energy. As disclosed in the present application, melanin provides some protection of fungal cells from very high doses of ionizing radiation and serves as an energy transducer in a metabolic process termed here as "radiosynthesis."

SUMMARY OF THE INVENTION

The present invention is directed to methods of enhancing the growth of an organism, such as for example a microorganism or plant, comprising increasing melanin content in the organism to generate a melanized organism and exposing the melanized organism to radiation to thereby enhance the growth of the organism.

The invention provides methods of reducing spread of radiation from radioactive materials comprising increasing melanin content in a microorganism to generate a melanized microorganism and applying the melanized microorganism to the radioactive material to thereby reduce the spread of radiation from the radioactive material. The invention further provides methods of reducing spread of radiation from a radioactive material comprising obtaining a melanin-containing microorganism and applying the melanin-containing microorganism to the radioactive material in an amount effective to reduce the spread of radiation from the radioactive material. The invention also provides methods of reducing spread of radiation from radioactive materials comprising obtaining a melanized organism, isolating melanin from the melanized organism, and applying the melanin to the radioactive material to thereby reduce the spread of radiation from the radioactive material.

The invention provides methods of protecting objects and subjects from radiation and/or from electronic pulses, where the methods comprise providing a melanized microorganism between the object or subject to be protected and a source of the radiation and/or electronic pulses. The invention also provides methods of protecting objects and subjects from radiation and/or from electronic pulses, where the methods comprise obtaining a melanized organism, isolating melanin from the melanized organism, and providing the melanin between the object or subject to be protected and a source of the radiation and/or electronic pulses.

The invention also provides melanized coatings and materials, methods of making melanized materials and coatings, and uses of the melanized materials and coatings.

DETAILED DESCRIPTION OF THE INVENTION

Figures 1A, 1B, 1C:
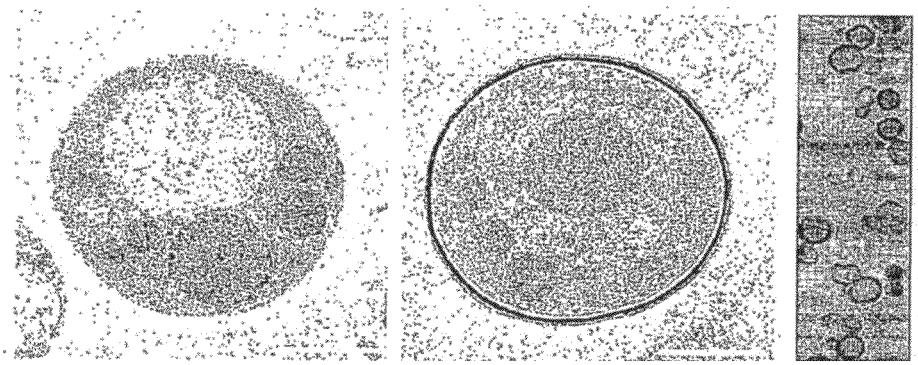
FIG. 1A-1C. Microscopic images of melanized fungal cells: A) TEM image of non-melanized *C. neoformans* cells; B) TEM image of melanized *C. neoformans* cells; C) light microscopy image of *C. neoformans* melanin "ghosts." Original magnification: TEM images-×13,000; light microscopy image-×1,000.

The present invention provides a method of enhancing the growth of an organism comprising increasing melanin content in the organism to generate a melanized organism and exposing the melanized organism to radiation to thereby enhance the growth of the organism. The organism can be, for example, a microorganism, a silk worm or a plant.

The invention provides a method of reducing spread of radiation from a radioactive material comprising obtaining a melanized microorganism and applying the melanized microorganism to the radioactive material to thereby reduce the spread of radiation from the radioactive material. The invention also provides a method of reducing spread of radiation from a radioactive material comprising obtaining melanin-containing microorganisms and applying the melanin-containing microorganisms to the radioactive material in an amount effective to reduce the spread of radiation from the radioactive material. The invention still further provides a method of reducing spread of radiation from a radioactive material comprising obtaining a melanized organism, isolating melanin from the melanized organism, and applying the melanin to the radioactive material to thereby reduce the spread of radiation from the radioactive material. As used herein, a "radioactive material" is a material that emits radiation. Examples of radioactive materials include, but are not limited to, materials from radiation spills, biomedical radioactive materials, and radioactive waste including waste from nuclear power plants and biomedical applications. Preferably, melanin encapsulates radioactive particles from the radioactive material, for example by binding nuclides or by incorporating them into melanin in a microorganism through a metabolic process.

The invention provides a method of protecting an object or a subject from radiation and/or from electronic pulses, where the method comprises providing a melanized microorganism between the object or subject to be protected and a source of the radiation and/or electronic pulses. The invention also provides a method of protecting an object or a subject from radiation and/or from electronic pulses, where the method comprises obtaining a melanized organism, isolating melanin from the melanized organism, and providing the melanin between the object or subject to be protected and a source of the radiation and/or electronic pulses. The melanized microorganism and/or the melanin can be fabricated in and/or on the source of the radiation and/or electronic pulses; and/or the melanized microorganism and/or the melanin can be fabricated in or on the object or subject to be protected from the radiation and/or electronic pulses.

The type of radiation can include, but is not limited to, one or more of ionizing radiation, gamma radiation, x-ray radiation, electromagnetic radiation, bremsstrahlung radiation, ultraviolet radiation, infrared radiation, and particulate radiation (e.g., α-radiation and β-radiation).

As used herein, a "melanized" organism means an organism in which the melanin content has been increased. The organism can constitutively synthesize melanin, or be an organism that does not constitutively synthesize melanin where melanization is induced, for example, by providing one or more genes required for melanin synthesis and/or the precursors for melanization.

The organism can be, for example, a microorganism, a silk worm or a plant. The microorganism can be, e.g., a bacterium, a plant, a protista, an algae or preferably a fungus. Suitable fungi include, but are not limited to, *Cryptococcus neoformans* and *Histoplasma capsulatum*.

One method of generating a melanized microorganism comprises growing the microorganism in the presence of a melanin precursor, for example one or more of L-dopa (3,4-dihydroxyphenylalanin), D-dopa, catechol, 5-hydroxyindole, tyramine, dopamine, tyrosine, cysteine, m-aminophenol, o-aminophenol, p-aminophenol, 4-aminocatechol, 2-hydroxyl-1,4-naphthaquinone, 4-metholcatechol, 3,4-dihydroxynaphthalene, gallic acid, resorcinol, 2-chloroaniline, p-chloroanisole, 2-amino-p-cresol, 4,5-dihydroxynaphthalene, 1,8-dihydroxynaphthalene, 2,7-disulfonic acid, o-cresol, m-cresol, and p-cresol. However, potential melanin precursors are not limited to this list since numerous compounds are known to serve as precursors for melanization. The precursor compound for melanization can be provided exogenously or synthesized by the organism.

The step of generating a melanized organism can also comprise transforming the organism with a gene that encodes melanin or with one or more genes involved in melanin biosynthesis. Genes involved in producing melanin have been described, e.g. [16, 34, 37-45]. Methods of transforming an organism with a gene are well known it the art, e.g. [35].

Another method of generating a melanized organism can also comprise exposing the organism to a factor that increases melanin production. For example, melanin production can be induced in an microbe by introducing a gene that encodes an enzyme that catalyzes the formation of melanin. For example, albino mutants of *C. neoformans* can be induced to produce melanin by inserting a gene for laccase [36]. The amount and type of melanin produced is influenced by the growth conditions, including nutrients, as shown for example in FIG. 4A-D.

The melanin can comprise for example one or more of allomelanin, pheomelanin and eumelanin. Eumelanins are derived from the precursor tyrosine. Pheomelanin is derived from the precursors tyrosine and cysteine. Allomelanins are formed from nitrogen-free precursors such as catechol and 1,8-dihydroxynaphthalenes. In one embodiment, the ratio of pheomelanin to eumelanin is at least 1:1. Preferably, the melanin contains divalent sulphur.

The radiation used to enhance the growth of the organism can comprise ionizing radiation. The radiation can be, for example, one or more of gamma radiation, x-ray radiation, solar radiation, cosmic radiation, electromagnetic radiation, bremsstrahlung radiation, ultraviolet radiation, infrared radiation, and particulate radiation (e.g., α-radiation and p-radiation). Preferably, the energy of the gamma radiation is lower than 50 kilo-electron Volt (keV). In one embodiment, the radiation does not include wavelengths of 300-400 nm.

The invention provides melanized organisms prepared by increasing melanin content in the organism to generate a melanized organism and exposing the melanized organism to radiation to enhance the growth of the organism. The invention further provides melanin isolated from the melanized organisms.

The melanized organisms can be used as a source of melanin, which can be added to materials or coatings such as paints. In addition, melanized microorganisms can be added to materials or coatings. The melanin can be in the form of a nanoshell comprising melanin. The nanoshell can comprise polymerized L-dopa, epinephrine, methyldopa, a substituted phenol derivative and/or a phenolic derivative that polymerizes into melanin. The nanoshell can comprises a nanosphere, a nanotube, a nanoellipsoid, a nanorod, a nanoball, or other suitable shape. The nanoshell can have a thickness of about 10 nm to about 1,000 nm. In one embodiment, the nanoshell has a thickness of about 100 nm. The nanoshells can be hollow, or filled with the same type of melanin as the shell or with a different type of melanin or with another material. Synthetic melanins can be used.

The invention provides a method of making a material comprising melanin, where the method comprises fabricating melanin into or onto the material and wherein the melanin is isolated from an organism whose growth has been enhanced by increasing melanin content in the organism to generate a melanized organism and exposing the melanized organism to radiation to thereby enhance the growth of the organism. The invention also provides a method of making a material comprising melanin, where the method comprises fabricating melanin into or onto the material and wherein the melanin is in the form of a melanized microorganism whose growth has been enhanced by increasing melanin content in the microorganism to generate a melanized microorganism and exposing the melanized microorganism to radiation to thereby enhance the growth of the microorganism.

The invention provides a melanin-based coating or material comprising a microorganism whose growth has been enhanced by increasing melanin content in the organism to generate a melanized organism and exposing the melanized organism to radiation to thereby enhance the growth of the organism. The invention also provides a melanin-based coating or material comprising melanin isolated from an organism whose growth has been enhanced by increasing melanin content in the organism to generate a melanized organism and exposing the melanized organism to radiation to thereby enhance the growth of the organism.

As an example of one application, melanin or melanized microorganisms can be used in paints or coatings that are applied to treat the foundation of a building or structure. The melanin or melanized organisms can also be fabricated into the building materials. Preferably, the melanin-based coating or foundation reduces entry of radon from soil into the building or structure.

The invention also provides energy transduction materials and energy storage materials comprising melanin.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Materials and Methods

*Microorganisms.* American Type Culture Collection (ATCC, Rockville, Md.) strain *C. neoformans* 24067 (serotype D) and CIB strain 1980 of *H. capsulatum* (a gift from A. Restrepo, Medellin, Colombia) were used in all experiments. *C. neoformans* was grown in Sabouraud dextrose broth (Difco laboratories, Detroit, Mich.) for 24 hrs at 30° C. with constant shaking at 150 rpm. *H. capsulatum* was grown with shaking at 37° C. in defined media consisting of 29.4 mM $KH_2PO_4$, 10 mM $MgSO_4 \times 7H_2O$, 13 mM glycine, 15 mM D-glucose, and 3 μM thiamine. Melanized *C. neoformans* and *H. capsulatum* cells were generated by growing the fungi in their respective media with 1 mM 3,4-dihydroxyphenylaianine (L-dopa) for 10 days. The cells were collected by centrifugation and washed three times with PBS, pH 7.2 before radiation exposure. *C. sphaerospermum* (ATCC, VA), an intrinsically melanized fungus was grown on Sabaroud dextrose agar (Becton, Dickinson and Company) for 15 days. To produce non-melanized cells of *C. sphaerospermum*, the agar was impregnated with 25 μg/mL tricyclazole, a compound that interferes with the pentaketide synthetic pathway of 5,6-dihydroxyindole (DHI)-melanin [1,5]. Cells grown with tricyclazole were light brown, indicating lower amounts of melanin, and further in the text are referred to as "melanin-deficient". The laboratory wild-type strain of *W. dermatitidis* 8656 {ATCC 34100 *[Exophiala dermatitidis* CBS 525.76]}, also an intrinsically melanized fungus, a strain with a disrupted polyketide synthase gene wdpks1Δ-1, and its complemented isolate (wdpks1Δ-1-501) were a gift from Dr. P. Szaniszlo (The University of Texas, Austin, Tex.). Routine propagation of these strains was in YPD [2% peptone, 1% Bacto Yeast extract, and 2% dextrose] at 37° C. with shaking at 150 rpm. Melanin from cuttlefish *S. officinalis* was purchased from Sigma.

Susceptibility of *C. neoformans* and *H. capsulatum* to external gamma radiation. Approximately $10^5$ melanized or non-melanized *C. neoformans* or *H. capsulatum* cells were placed in microcentrifuge tubes in 0.5 mL PBS and irradiated with a $^{137}Cs$ source at a dose rate of 14 Gy/min. The cells were exposed to doses of up to 220 Gy. The exposures of 1,000-8,000 Gy were given by irradiating the cells at 30 Gy/min. Following radiation exposure, $10^3$cells from each tube were plated in agar to determine viability as measured by colony forming units (CFUs). Alternatively, non-melanized *C. neoformans* cells were irradiated at 14 Gy/min in the presence of 0.02 or 0.4 mg of powdered *S. officinalis* melanin or in the presence of 0.01 or 0.1 mg of *C. neoformans* melanin "ghosts" intact or crushed in agate mortar, followed by determination of viability as measured by CF-Us. Their viability was compared to that of melanized and non-melanized *C. neoformans* irradiated under the same conditions. Hollow melanin shells which remain after the treatment of melanized cells with enzymes, guanidinium isothiocyanate and 6 M HCl were dubbed "ghosts" because they preserved the shape of the cells.

Exposure of fungi to ionizing radiation in conditions of limited nutrients supply. *C. sphaerospermum* was used in preliminary experiments. Melanized and non-melanized (tricyclazole-treated) cells of *C. sphaerospermum* were grown on BBL Sabouraud dextrose agar for 15 days, harvested and plated on water agar prepared by mixing agar powder with minimal media lacking glucose. Four-sectional, 100×15 mm dishes were used. Identical plates were made for irradiated and control samples. Five mL of this agar was added to each of the left two sections of each plate. These sections were called "no sucrose" sections. Five mL volumes of sucrose-containing agar (prepared by mixing agar powder with 100 mg/L sucrose as described in [6] and with minimal media lacking glucose) was added to the right two sections of each plate. Non-melanized *C. sphaerospermum* was added to the top compartments and melanized *C. sphaerospermum* was added to the bottom compartments of each plate. Agar in the top compartments where non-melanized *C. sphaerospermum* was plated contained 25 μg/mL tricyclazole to inhibit melanization. Approximately 20 cells per section were plated. All plates were prepared in duplicate. The plates were wrapped in foil and exposed continuously to a radiation field of 0.05 mGy/hr created by 188Re/188W isotope generator for 15 days while control plates were exposed only to background radiation ($10^{-4}$ mGy/hr). The colonies were counted and measured daily.

*W. dermatitidis* was used in subsequent experiments. Before every radiation exposure experiment the wild type, albino mutant and complemented strain were cultured in a following manner using the modified procedure from [33]: frozen cells were diluted and cultured in 20 mL YPD at 37° C. while shaken at 150 rpm for 48 hrs, then diluted to $10^6$ cells/mL and grown for another 48 hrs. At the end of the $2^{nd}$ 48 hrs period both wild type and complemented strains developed dark coloration while albino mutant cells were light yellow. The cells were then diluted back to $10^6$ cells/mL and cultured for 24 hrs; this procedure was repeated for another 24 hrs. Finally, the cells were diluted and grown for 24 hours in media with pH of 6.5 containing essential salts (3 g/L $NaNO_3$, 1 g/L $K_2HPO_4$, 1 g/L $MgSO_4.7H_2O$, 0.5 g/L KCl, 0.003 g/L thiamine, 5.3 g/L NH$_4$Cl) and supplemented with 120 mg/L sucrose as a carbon source. The wild-type and complemented strains maintained their dark color while albino mutant was light yellow.

Following the growth procedure outlined above, the cells were washed twice in the medium described above, and their concentration was adjusted to 5×10$^5$ cells/mL in the same medium. One ml aliquots in 1.5 ml microfuge tubes were placed at 37° C. in the dark without shaking, either in the cell incubator with the background level of radiation or in a radiation field of 0.05 mGy/hr created by 188Re/188W isotope generator. For each time point, triplicate samples were used. After 8, 16, 22 and 30 hrs of exposure the cells were diluted and plated on YPD agar, grown for 4 days at room temperature, and CFUs were counted. To determine the effect of "radiation withdrawal" on cell growth in one experiment the cells were grown for 8 hrs in the 0.05 mGy/hr radiation field, then incubated for an additional 14 hrs at the background level of radiation, plated and CFUs were counted. The cells enter stationary phase after 30 hrs.

Influence of growth media on the chemical composition of *C. sphaerospermum* melanin. Approximately 1,000 *C. sphaerospermum* cells were plated on different media: water agar impregnated with minimal media (no glucose) and casein, water agar impregnated with minimal media (no glucose) and 40 g/L dextrose, potato dextrose agar (Becton, Dickinson and Company), potato dextrose agar impregnated with 25 ug/mL tricyclazole, and Sabaroud dextrose agar.

Determination of metabolic activity of melanized and non-melanized *C. neoformans* cells subjected to ionizing radiation or different temperatures by XTT and MTT assays. Melanized and non-melanized *C. neoformans* cells were washed, suspended in PBS and their concentration was adjusted to 10 per mL. To account for the possibility of melanin itself changing the reaction through electron transfer or solubility/retention of formazan product, the aliquots of both melanized and non-melanized cells were heat-killed at 65° C. (water bath) for one hour and used as controls. 10$^7$ cells were placed into the wells in 96 well plates, 5 wells per each condition. The plates were covered with foil to exclude any light effects and incubated overnight at room temperature (22° C.), at 30° C., or at 30° C. in a constant radiation field of 0.05 mGy/hr. For XTT (2,3-bis(2-methoxy-4-nitro-5-sulfophenyl)-5-[(phenylamino) carbonyl]-2H-tetrazolium hydroxide) assay 54 µL (XTT)/menadinone was added to each well, the plates were covered with foil, shaken for 2 minutes, and incubated at 30° C. The absorbance was read at 492 nm (Labsystem Multiskan, Franklin, Mass.). For MTT (2-(4,5-dimethyl-2-thiazolyl)-3,5-diphenyl-2H-tetrazolium bromide) assay, the MTT solution in PBS was added to the wells with the cells, so that the final MTT concentration became 0.5 mg/mL. After incubation at 37° C., the contents of the wells were spun down at 2,000 rpm, supernatant was discarded, followed by addition of 200 µl 0.04 M HCl in absolute isopropanol to each sample. The samples were transferred into the 96-well plate and the absorbance was read at 550 nm.

Exposure of *C. neoformans* to ionizing radiation under limited nutrient conditions, $^{14}$C-acetate incorporation and dry weight measurements. H99 wild type and Lac(−) mutant cells were grown as above. Melanization of H99 was achieved by incubation in 1 mM L-Dopa/minimal medium (1/200) in the dark at 30° C., at 150 rpm. The cells were washed with essential salts solution (3 g/L NaNO$_3$, 1 g/L K$_2$HPO$_4$, 1 g/L MgSO$_4$.7H$_2$O, 0.5 g/L KCl, 0.003 g/L thiamine, 5.3 g/L NH$_4$Cl), pelleted and taken up in 1 mM Na acetate solution in essential salts spiked with 0.1 µCi/mL $^{14}$C-acetate. The cell concentration was adjusted to 10$^5$ cells/ml, 1 mL samples of each strain were placed in 1.5 mL Eppendorf tubes (4 samples per time point) and subjected either to the background level of radiation or to a radiation field of 0.05 mGy/hr created by 188Re/188W isotope generator for up to 30 hr at 30° C. The cell uptake of $^{14}$C-acetate was quantified by counting the tubes in a scintillation counter, spinning cells, separating supernatant and counting the cell pellet again. The cells were also plated for CFUs. For dry weight experiments 5 mL of cells at 4×10$^7$ cells/mL cell density were irradiated for 20 hr at 30° C., filtered through pre-weighted 0.2µ filters, the filters were carefully dried and weighted again.

Isolation and purification of fungal melanins. The *C. neoformans* and *H. capsulatum* melanized cells were grown as above. *C. sphaerospermum* cells were grown on different media as described above. *W. dermatitidis* cells were grown on YPD. The cells were suspended in 1.0 M sorbitol-0.1 M sodium citrate (pH 5.5). Lysing enzymes (Sigma Chemical Co.) were added to the suspension at 10 mg/mL and the suspensions were incubated overnight at 30° C. Protoplasts were collected by centrifugation, and incubated in 4.0 M guanidine thiocyanate overnight at room temperature. The resulting particulate material was collected by centrifugation, and the reaction buffer (10.0 mM tris, 1.0 mM CaCl$_2$, 0.5% SDS) was added to the particles. Proteinase K was added to the suspension at 1.0 mg/mL followed by overnight incubation at 37° C. The particles were boiled in 6.0 M HCl for 1 hour. Finally, the resulting material ("ghosts") was washed with PBS, dialyzed against deionized water for 2 days and dried in air at 65° C. overnight. The yield of melanized cells per 1 liter of medium is 2 g and the yield of purified ghosts is 0.3 g.

Transmission electron microscopy (TEM). The *C. neoformans* and *C. sphaerospermum* "ghosts" were frozen under high pressure using a Leica EMpact High Pressure Freezer (Leica Microsystems, Austria). Frozen samples were transferred to a Leica EM AFS Freeze Substitution Unit and freeze substituted in 1% osmium tetroxide in acetone. They were brought from −90° C. to room temperature over 2-3 days, rinsed in acetone and embedded in Spurrs epoxy resin (Polysciences, Warrington, Pa.). Ultrathin sections of 70-80 nm were cut on a Reichert Ultracut UCT, stained with uranyl acetate followed by lead citrate and viewed on a JEOL (Tokyo, Japan) 1200EX transmission electron microscope at 80 kV.

Oxidation of melanins and HPLC of oxidized melanins. The melanin "ghosts" were subjected to acidic permanganate oxidation as described in [20-23]. The pyrrole-2,3,5-tricarboxylic acid (PTCA), pyrrole-2,3-dicarboxylic acid (PDCA), 1,3-thiazole-2,4,5-tricarboxylic acid (TTCA) and 1,3-thiazole-4,5-dicarboxylic acid (TDCA) used as standards were a gift from Dr. K. Wakamatsu of Fujita Health University of the Health Sciences, Toyoake, Japan. The oxidation products were analyzed by high pressure liquid chromatography (HPLC) using a Shimadzu LC-600 liquid chromatograph, Hamilton PRP-1 C$_{18}$ column (250×4.1 mm dimensions, 7 µm particle size), and Shimadzu SPD-6AV UV detector. The mobile phase was 0.1% trifluoroacetic acid in water (solvent A) and 0.1% trifluoroacetic acid in acetonitrile (solvent B). At 1.0 mL/min, the elution gradient was (min, % B): 0, 0; 1, 0; 12, 25; 14, 25; 16, 0. The UV detector was set at a 255 nm absorbance.

MALDI mass spectrometry. The major peaks generated during chromatography of oxidized melanins were collected and analyzed by MALDI-TOF mass spectrometry in positive pressure mode on PE-Biosystems Mariner ESI TOF mass spectrometer. Peptide mixture with molecular weights of 1059.56, 1296.68 and 1672.95 in 2,5-dihydroxybenzoic acid matrix was used for calibration.

Electron spin resonance spectroscopy (ESR). The ESR of melanin "ghosts" was performed on ER 200D EPR/ENDOR spectrometer with ESP 300 upgrade (Brucker Instruments, Inc. Billerica, Mass. ESR spectra were obtained by suspending "ghosts" in water. ESR spectra of C. neoformans ghosts were obtained in dry state before and after irradiation with 0.3 kGy dose and after subsequent suspension in water.

NADH-ferricyanide reaction in presence of untreated and irradiated C. neoformans melanin. The ability of melanin to oxidize or reduce NADH and ferricyanide was determined spectrophotometrically as in [28]. The absorbance of NADH was monitored at 340 nm and absorbance of ferricyanide at 420 nm. Fifty μg of C. neoformans melanin was used in the reactions; dry melanin was subjected to 20 and 40 min irradiation with 137-Cs source at a dose rate of 14 Gy/min; put into dry ice following irradiation and taken up in the ferricyanide solution immediately before measurements.

Determination of metabolic activity of melanized and non-melanized C. neoformans cells at different temperatures. Melanized and non-melanized C. neoformans cells were washed, re-suspended in PBS and their concentration was adjusted to $10^8$ per mL. For control, aliquots of both melanized and non-melanized cells were heat-killed at 65° C. (water bath) for one hour. $10^7$ cells were placed into the wells in 96 well plates, 5 wells per each condition. The plates were covered with foil and incubated overnight, one at room temperature (22° C.), and the other at 30° C. Fifty 1 L of 1 mg/mL 2,3-bis(2-methoxy-4-nitro-5-sulfophenyl)-5-[(phenylamino) carbonyl]-2H-tetrazolium hydroxide (XTT) in PBS and 4 μL of 1 mM menadinone in acetone were added to each well, the plates were covered with foil, shaken for 2 minutes, and incubated for 5 hours at room temperature and 30° C., respectively. The absorbance was read at 570 nm (Labsystem Multiskan, Franklin, Mass.).

Calculation of linear attenuation coefficient. The reduction in radiation intensity was calculated from the linear parts of Cn and Hc survival curves assuming that 10% increase in survival is equivalent to 10% decrease in radiation intensity.

Calculation of dose reduction factor (DRF). DRF was calculated according to the formula:

$$\text{DRF} = \text{(Dose needed to cause effect with protector)} / \text{(Dose needed to cause effect without protector)} \quad (1).$$

Calculation of colonies volume. The Volume of half-sphere was calculated as:

$$V/2 = \pi/12\, d^3 \quad (2).$$

Calculation of linear growth rate. Radial linear growth rate of C. sphaerospermum colonies was calculated as:

$$K = (R_t - R_o)/(t - t_o) \quad (3),$$

where K is radial linear growth rate, mm/hr; and $R_t$ and $R_o$ are colony radii at time t and time $t_o$, respectively.

Energy balance of Compton scattering. Energy was calculated as:

$$E_o = E_{re} + E_{sc} \quad (4),$$

where $E_{re}$ is the energy of recoil electron, and $E_o$ and $E_{sc}$ are the energies of the incident and scattered photons, respectively.

Probability of scattering depending on the angle of incident photon. The amount of energy transferred to the recoil electron in Compton scattering ranges from nearly zero for $\theta = 0°$ ("grazing" collisions) up to some maximum value $E_{re}^{max}$ that occurs in 180° backscattering events.

$$E_{sc} = E_o/[1 + (E_o/511)(1 - \cos\theta)] \quad (5),$$

where $E_o$ and $E_{sc}$ are the incident and scattered photon energies in keV, respectively. For high-energy photons the probability of scattering is highest for the low scattering angles [14]. For example, when a 662 keV photon emitted by 137-Cs source scatters at 30°, its energy will decrease to 470 keV, and approximately 10 subsequent scattering events at the same angle would reduce the photon energy to a level when the photoelectric effect can occur.

Statistical analysis. The slopes of the survival curves were determined by linear regression (GraphPad PRISM software, San Diego, Calif.) and a Student's test for unpaired data was performed to analyze the differences in survival. Differences were considered statistically significant when P values were <0.05.

Results

To investigate the hypothesis that melanin makes fungi more resistant to radiation damage, two fungi capable of melanogenesis were analyzed, C. neoformans and H. capsulatum. These fungi were selected for study because they can be grown in either non-melanized or melanized states for comparative purposes (FIG. 1A-1B). The fungal cell walls became melanized when grown with Ldopa (3,4-dihydroxyphenylalanin) (FIG. 1B). Previous work [11] as well as this study showed that all melanin in the cells is concentrated in the cell wall where it is assembled into multiple concentric layers of approximately 100 nm thickness consisting of closely packed much smaller particles [12]. Melanin particles of hollow spherical shape can be isolated from melanized cells by digestion in concentrated acid and have been dubbed "ghosts" because they retain the shape and dimensions of the parent cell (FIG. 1C).

Figure 2A:
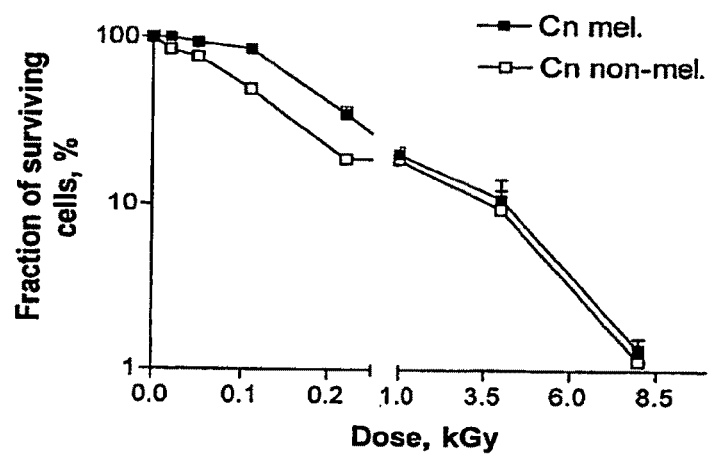
FIG. 2A-2D. Survival of non-melanized and melanized fungal cells following exposure to external gamma rays. A) *C. neoformans* in PBS up to 220 Gy at 14 Gy/min and up to 8,000 Gy at 30 Gy/min; B) *H. capsulatum* in PBS up to 220 Gy at 14 Gy/min and up to 8,000 Gy at 30 Gy/min; C) melanized and non-melanized *C. neoformans* irradiated at 14 Gy/min up to 400 Gy, 0.02 or 0.4 mg of *S. officinalis* melanin was added to non-melanized cells; D) melanized and non-melanized *C. neoformans* irradiated at 14 Gy/min up to 200 Gy, 0.01 or 0.1 mg of intact or crushed *C. neoformans* melanin "ghosts" was added to samples. rad—irradiated, ctrl—control, mel—melanized.
Figure 2B:
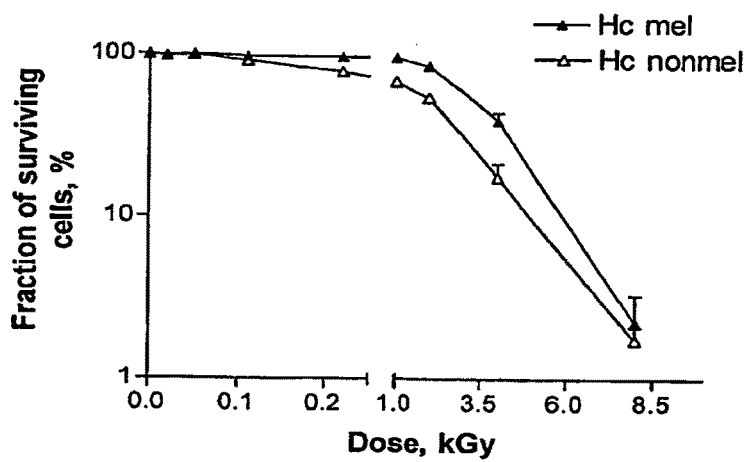

Melanized and non-melanized C. neoformans and H. capsulatum cells were subjected to very high doses of radiation—up to 8,000 Gy. For comparison, 5 Gy is lethal to humans. Since the $LD_{10}$ for these organisms in their non-melanized form is around 50-100 Gy [13], high doses were needed to analyze the radioprotective effect of melanin. Melanized C. neoformans cells were significantly less susceptible to external gamma radiation (P=0.01) in the dose range of 0-220 Gy than non-melanized cells (FIG. 2A) with dose reduction factor (DRF) (Equation 1) calculated to be 1.6 while at 1,000-8,000 Gy the protective effects were not statistically significant (P=0.4). For H. capsulatum cells melanin provided protection up to 8,000 Gy (P<0.01) with DRF of 1.6 (FIG. 2B).

To estimate the radioprotective properties of melanin, its effective linear attenuation coefficient (μ) and effective half value layer (HVL) were calculated according to the equations:

$$I = I_o e^{-\mu x} \quad (6)$$

$$\text{HVL} = 0.693/\mu, \quad (7)$$

where $I_o$ and I are, respectively, the radiation intensities incident and transmitted through an absorber of thickness x (in cm) and μ is linear attenuation coefficient (in cm$^{-1}$) and HVL is the half-value layer. For H. capsulatum melanin μ and HVL were found to be $1.4 \times 10^4$ cm$^{-1}$ and 0.5 μm, respectively; and for C. neoformans—$1.1 \times 10^4$ cm$^{-1}$ and 0.6 μm. For comparison, the linear attenuation coefficient of lead is 27 cm$^{-1}$ [14].

To elucidate the contribution of the nanospherical arrangement of melanin in fungal cells to radioprotection, non-melanized C. neoformans cells were irradiated with doses of up to 400 Gy in the presence of melanin from Sepia officinalis (cuttlefish), which is not arranged in hollow spheres, in amounts equal or 20 times higher than the amount of melanin in the same number of melanized C. neoformans cells. S.

Figure 2C:
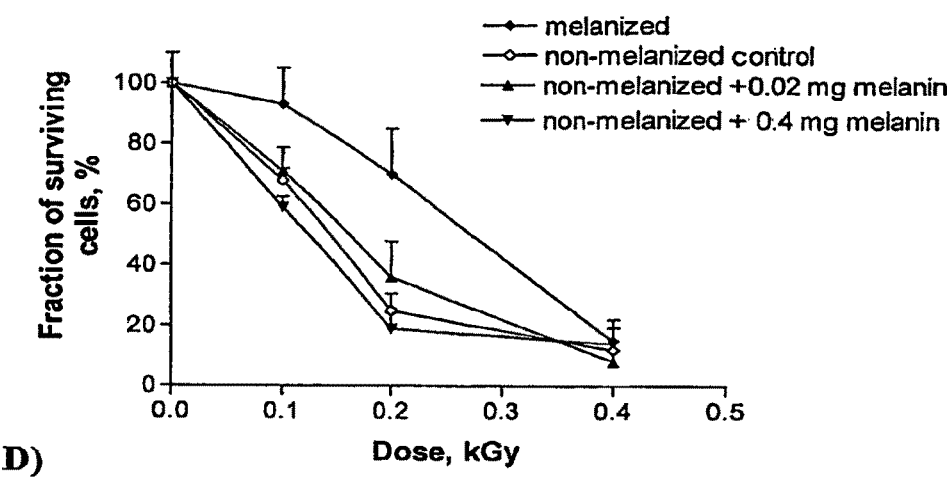
Figure 2D:
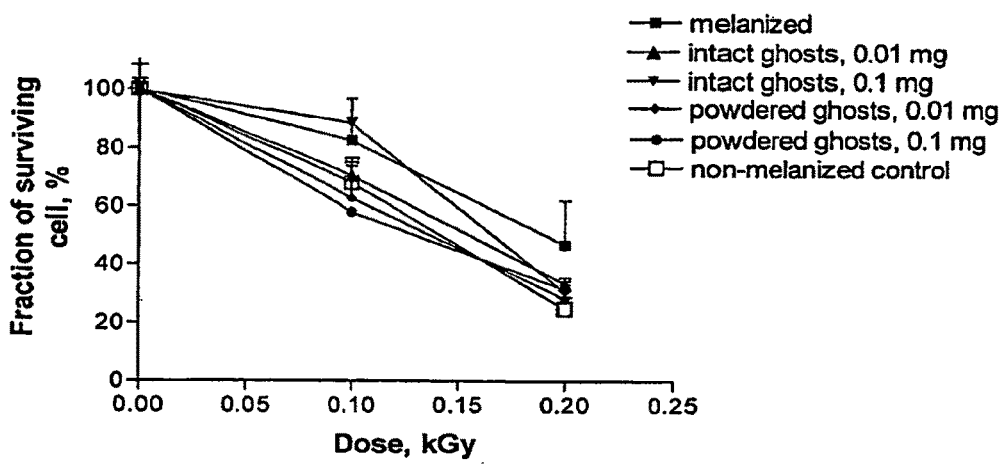

*officinalis* melanin conferred no protection at any dose (FIG. 2C), suggesting that the spatial arrangement of melanin particles in the 'ghosts' was important in radioprotection. To exclude the possibility that differences in chemical composition of fungal and *S. officinalis* melanins accounted for the lack of radioprotection by the latter, the experiment was modified by irradiating non-melanized *C. neoformans* cells with the same amounts of intact and powder-crushed melanin "ghosts" (FIG. 2D). 0.1 mg intact "ghosts" protected the cells up to 120 Gy in the same way as melanization, while crushed "ghosts" afforded only slight protection. Hence, when melanin is arranged in nanospheres, it scatters/absorbs radiation more efficiently than powdered melanin of the same chemical composition.

The ability of melanized fungi to utilize ionizing radiation as an energy source in conditions of limited nutrient availability was first investigated using the intrinsically melanized fungus *Cladosporium sphaerospermum*. This organism was selected for study because it is a dominant species inhabiting the damaged reactor at Chernobyl [6]. The fungus was placed in a constant radiation field of 0.05 mGy/hr, a non-fungicidal dose range comparable to that of the Chernobyl reactor [6]. Water agar was also supplemented with minimal media containing sources of carbon and mineral salts, and, in one condition, with limited amount of sucrose as a conventional energy source.

Figure 3A:
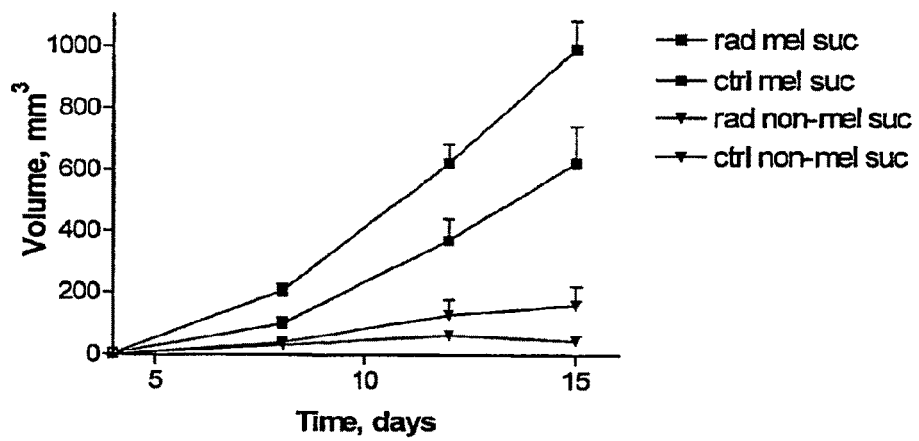
FIG. 3A-3D. Survival of non-melanized and melanized *C. sphaerospermum* cells following exposure to external gamma rays. Average volume (A, B) and radial growth rate (C, D) of melanized and melanin-deficient *C. sphaerospermum* colonies grown on agar plates with (A, C) or without sucrose (B, D) in radiation field of 0.05 mGy/hr or at background radiation level (control). rad—irradiated, ctrl—control, mel—melanized, suc—sucrose added.
Figure 3B:
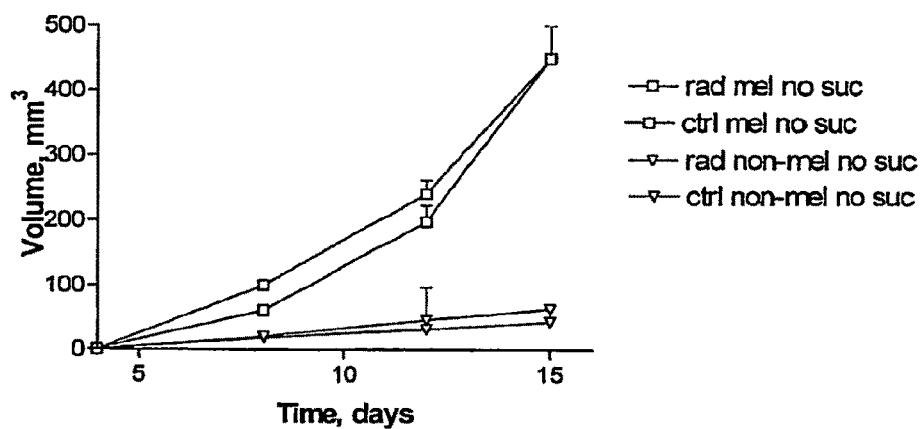
Figures 3C, 3D:
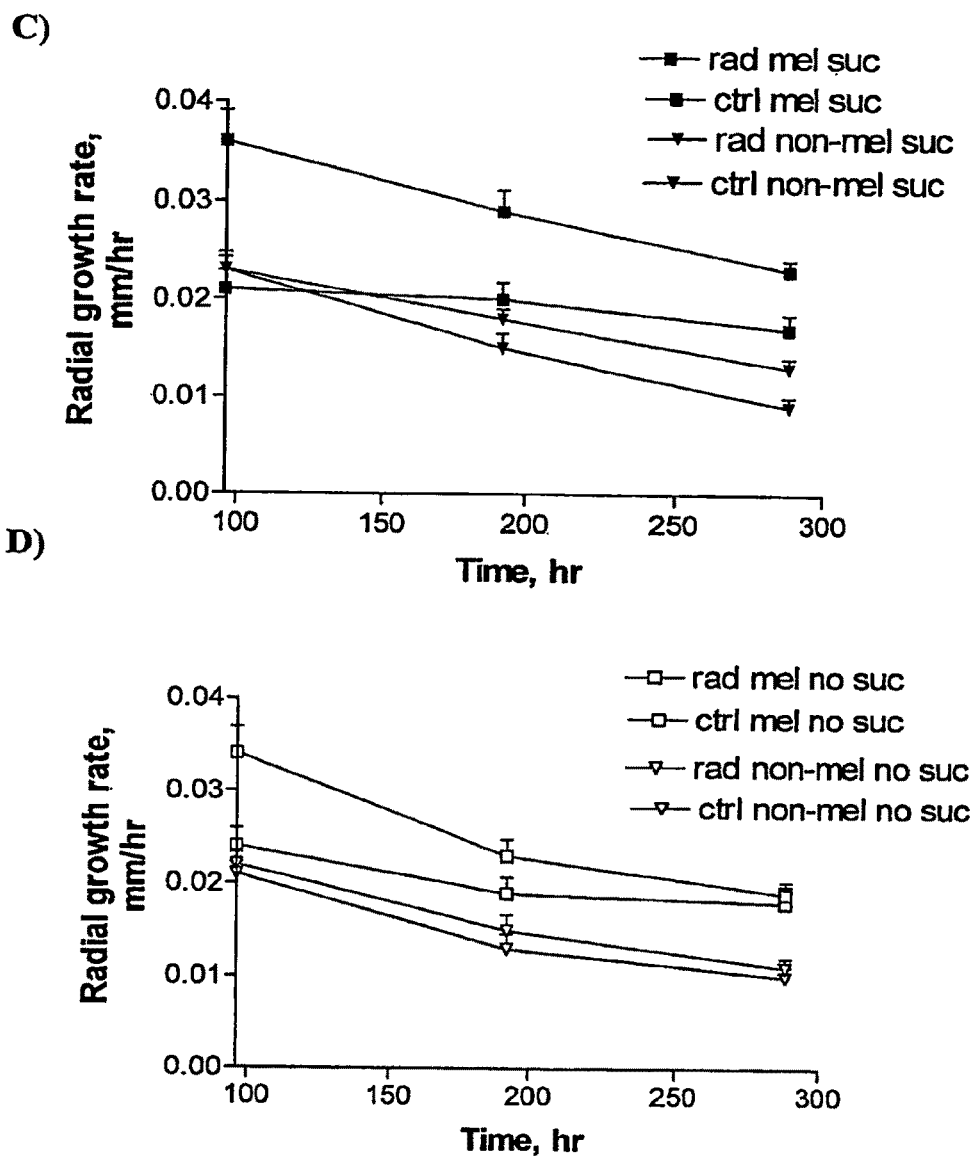
Figure 4A:
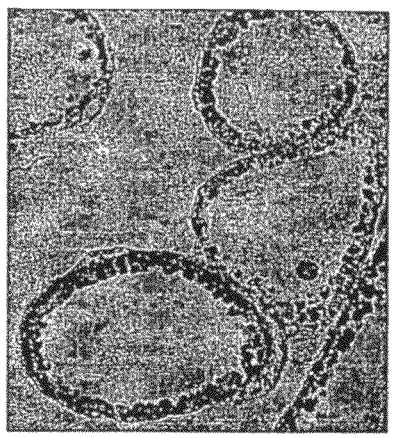
FIG. 4A-4D. TEM images of *C. sphaerospermum* "ghosts" of cells grown on nutrient rich or nutrient-deficient media. A) potato dextrose agar; B) Sabaroud dextrose agar; C) water agar with casein; D) water agar with dextrose. Original magnification—×13,000.
Figure 4B:
Figure 4C:
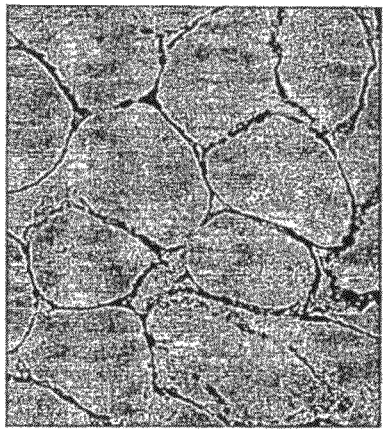
Figure 4D:
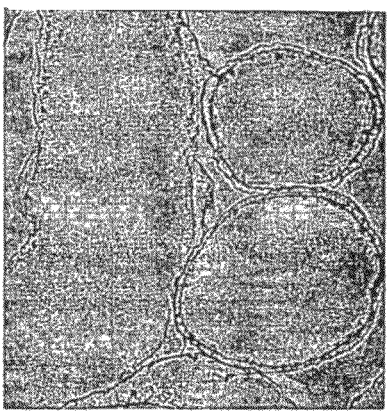

Using agar with sucrose, the irradiated melanized colonies of *C. sphaerospermum* grew significantly more in regard to their volume and faster as shown by their radial growth rate (Equations 2 and 3) than control melanized or control melanin-deficient ones (FIG. 3). Irradiated melanized colonies grew more than irradiated melanin-deficient cells, consistent with radiosynthesis and invalidating the possible argument that radiation simply induced agarase in fungi—an enzyme that breaks down agar into possible nutrients, or that radiation altered the agar to provide nutrients. The same trend was observed for cells grown without sucrose—the largest and fastest growing colonies were observed for irradiated melanized cells in comparison with the other 3 controls. All colonies grown without sucrose were smaller than those grown with this nutrient.

In the absence of sucrose at Day 15, the volume and linear growth rate for irradiated melanized and control melanized cells equalized. Possible explanation of this phenomenon comes from analyzing transmission electron microscopic images of *C. sphaerospermum* "ghosts" grown on media containing different substrates which revealed differences in thickness of the melanin layer (FIG. 4). The thickest layers were observed for cells grown on nutrient-rich potato dextrose agar while cells grown on water agar impregnated with dextrose had only thin melanin coatings. It is possible that the melanin layer surrounding the cells grown in the conditions of complete starvation was too thin to utilize efficiently the energy of ionizing radiation. This effect became apparent at the end of the observation period (15 days) when all internal reservoirs of nutrients in the cells were depleted and no melanin could be produced. This finding reinforces the conclusion that melanin is required for radiosynthesis.

The conclusion from these experiments is that melanin was produced by fungi even when the amounts of nutrients and energy sources in the media were very low or absent; and the combination of melanized cells and radiation produced increased growth of colonies in all conditions when chemical energy resources were limited or absent. One limitation of this system, however, was the need to generate non-melanized cells of *C. sphaerospermum* by treating them with tricyclazole—a compound that interferes with the pentaketide synthetic pathway of 1,8-dihydronaphthalene (DHN)-melanin [1,5] and which might also affect the metabolic processes in fungi. Another limitation of *C. sphaerospermum* is the fact that hyphal cells of this fungus often aggregate and one cannot measure growth by standard CFUs. Although the results showing colony radial growth were suggestive of increased fungal mass they were not conclusive because larger colonies could conceivably have resulted from differences in cellular packing or swelling. Hence, a different system was sought that would allow confirmation of these findings. *Wangiella dermatitidis*, an intrinsically melanized human pathogenic fungus that exists predominantly as a yeast form in vitro, was selected. Recently, an albino strain of *W. dermatitidis* (wdpks1Δ-1) which lacks the primary gene WdPKS1 responsible for generating melanin, a polyketide synthase, and also an isolate (wdpks1Δ-1-501) complemented with wild type wdpks1 gene have become available [16]. The availability of this fast-growing fungus, which also produces very few multicellular forms in vitro in comparison with *C. sphaerospermum*, allowed quantification of the effect of radiation on cell growth by counting CFUs instead of measuring colonies diameter.

Figure 5A:
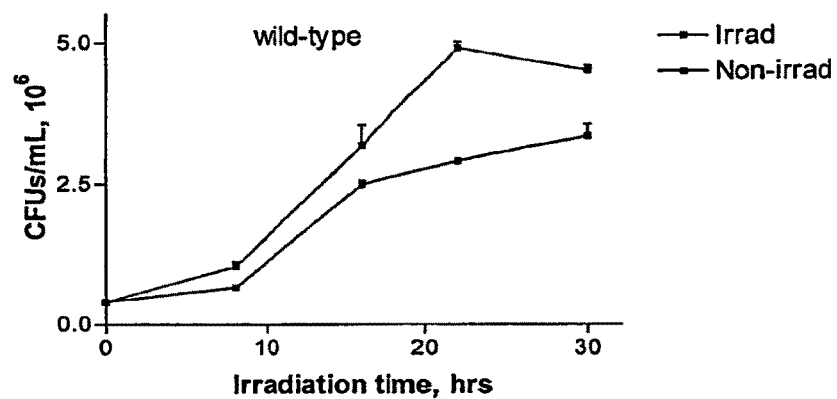
FIG. 5A-5D. Growth of *W. dermatitidis* wild type 8656 (A), albino mutant wdpks1Δ-1 with a disrupted polyketide synthase gene (13) and a strain complemented with wild type gene wdpks1 (C) under conditions of limited nutrients supply in radiation field of 0.05 mGy/hr or at background radiation level. The cells were exposed to radiation for various times and plated for CFUs on YPD. Panel D shows an experiment where *W. dermatitidis* was exposed to radiation for 8 h and then grown in the absence of radiation for the subsequent 14 h. Irrad—irradiated, non-irrad—non-irradiated.
Figure 5B:
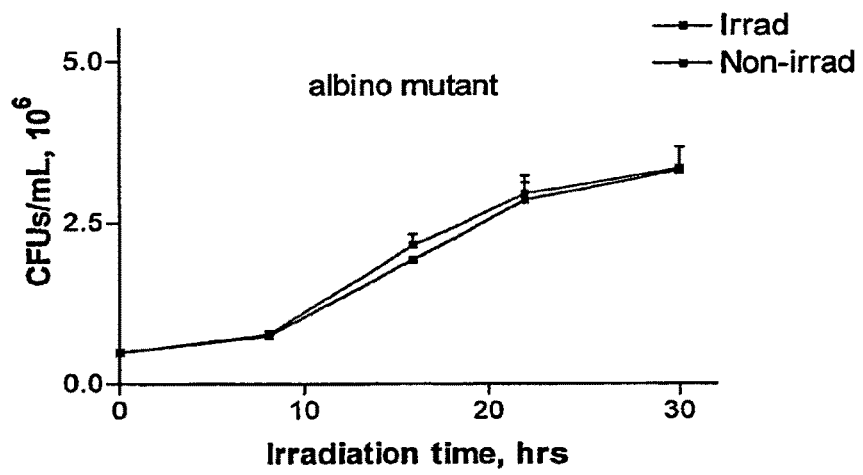
Figure 5C:
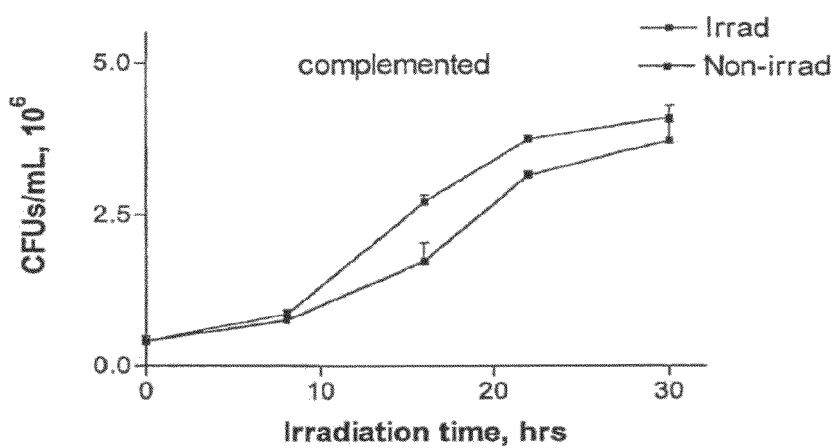
Figure 5D:
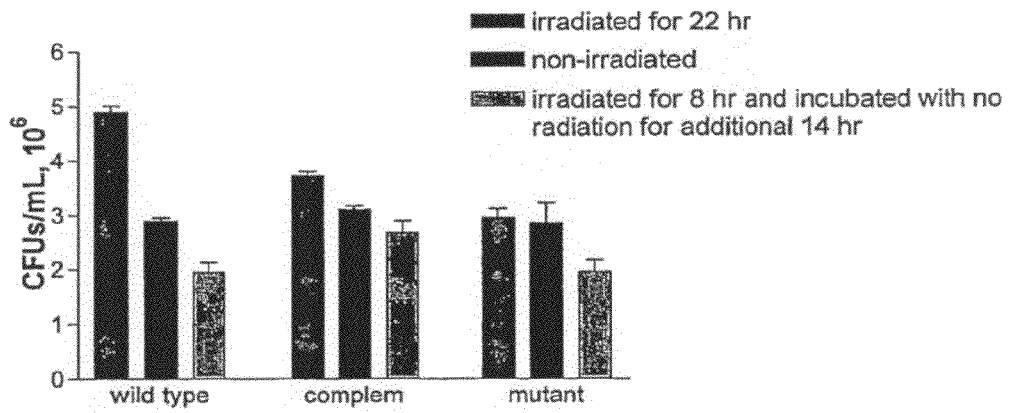

Exposure of melanized wild type, mutant and complemented *W. dermatitidis* cells to ionizing radiation resulted in significantly more cells being produced as measured by CFU for the melanin producing strains ($P<0.01$) than for the non-irradiated melanized control cells or the irradiated wdpks1Δ-1 albino mutant strain at 8, 16, 22 and 30 hrs for wild type cells (FIG. 5A) and for 16 and 22 hr time points for complemented strain (FIG. 5C). There was also a trend towards more colonies for the irradiated complemented strain at 30 hr in comparison with the non-irradiated control ($P=0.05$). The observation of this effect for both wild type and complemented strain implicates melanin in the phenomenon of promoting growth in the presence of radiation. At 16, 22, and 30 hr of irradiation the two melanin-containing strains of *W. dermatitides* had more colonies than the amelanotic mutant strain. In contrast, there was no growth difference between the three strains in the absence of irradiation. Some increased growth observed in irradiated albino mutant in comparison with non-irradiated albino cells at 16 hrs (FIG. 5B) can be explained by the well documented phenomenon that very low doses of ionizing radiation can stimulate cell proliferation [17, 18]. When the cells of all three strains were exposed to radiation for 8 hrs and then grown without radiation for an additional 14 hrs, the withdrawal of radiation was followed by decreased growth in comparison to those cells exposed to radiation for the whole 22 hrs or grown without radiation for 22 hr. The difference in CFUs was most pronounced for the wild type cells (2.5-fold as compared to irradiated cells). This experiment also rules out an explanation of growth differences based on stimulation of cell proliferation alone, which would have resulted in higher number of cells in the samples that were withdrawn at 8 hrs relative to the non-irradiated controls. The doubling times for *W. dermatitidis* served as additional proof of efficient utilization of ionizing radiation by melanized cells as they were significantly shorter for irradiated wild type and complemented cells in comparison with non-irradiated controls while there were no differences for albino mutants (Table 1). Overall, these findings reinforce the conclusion that melanized fungi are capable of utilizing ionizing radiation in their metabolism via radiosynthesis.

TABLE 1

Doubling times* for *W. dermatitidis* grown in nutrient-deficient medium with and without radiation. The means and SEM of 4 experiments are presented.

| | Doubling time, hr | | |
|---|---|---|---|
| strain | irradiated | control | P value** |
| wild type | 6.5 (0.1) | 7.4 (0.2) | 0.02 |
| mutant | 9.8 (1.0) | 10.8 (1.8) | 0.7 |
| complemented | 6.8 (0.1) | 7.3 (0.1) | 0.01 |

*Doubling time = ln 2/((ln(A/A$_o$)/t), where A - amount of cells at time t, A$_o$ - amount of cells at time 0.
**unpaired t-test was performed for each strain to compare doubling times for irradiated and control samples.

Figures 6A, 6B:
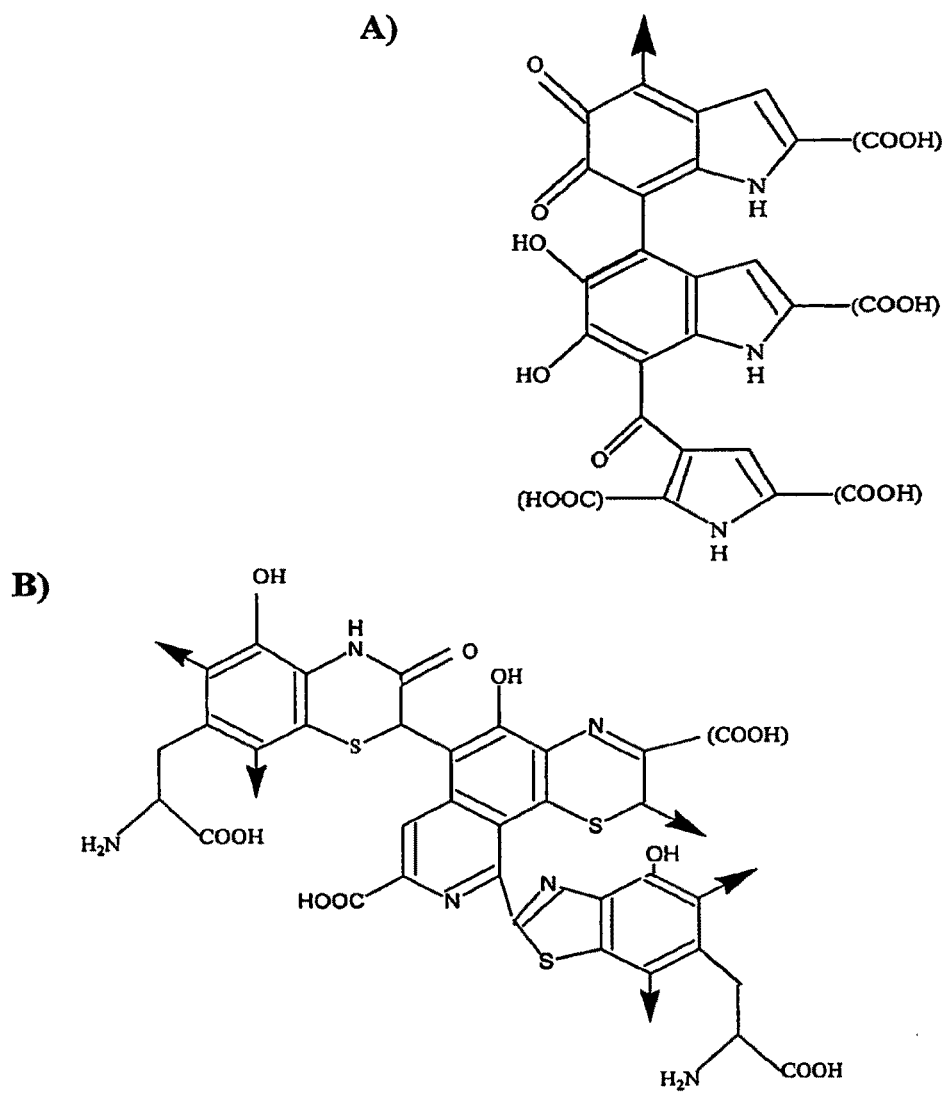
FIG. 6A-6H. HPLC of permanganate-oxidized melanins. A) Structure of eumelanin oligomer; B) structure of pheomelanin oligomer. Chromatograms of C) background solution, D) *C. neoformans*, E) *H. capsulatum*, F) Sepia officinalis, G) *C. sphaerospermum* grown on Sabaroud dextrose agar, and H) *W. dermatitidis* isolate 8656 (wild type). PDCA—pyrrole-2,3-dicarboxylic acid; PTCA—pyrrole-2,3,5-tricarboxylic acid; TTCA—1,3-thiazole-2,4,5-tricarboxylic acid; TDCA—1,3-thiazole-4,5-dicarboxylic acid. Absorption was monitored at 255 nm and displayed on the linear scale.
Figure 6C:
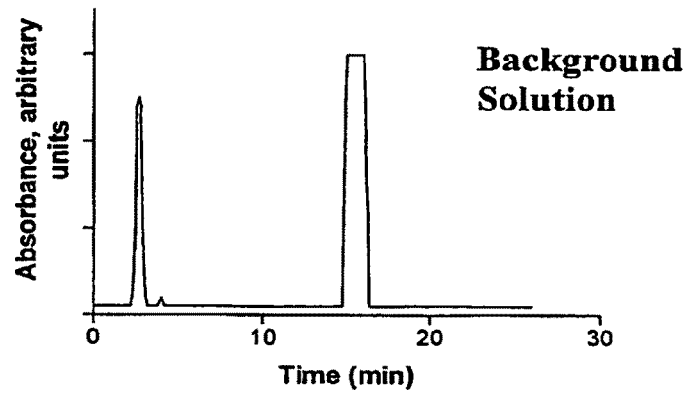
Figure 6D:
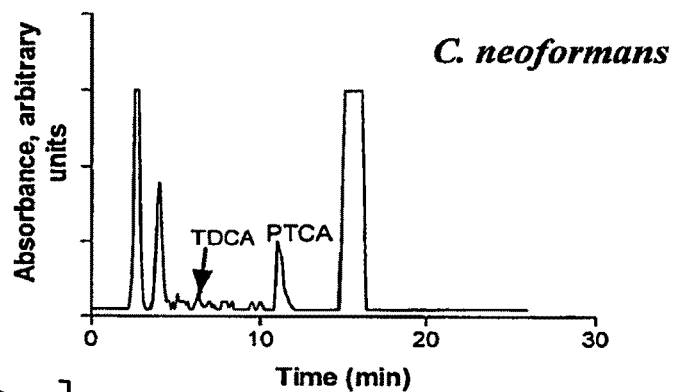
Figure 6E:
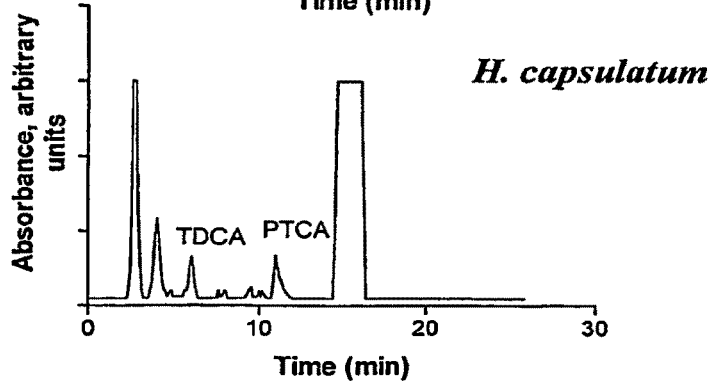
Figures 6F, 6G, 6H:
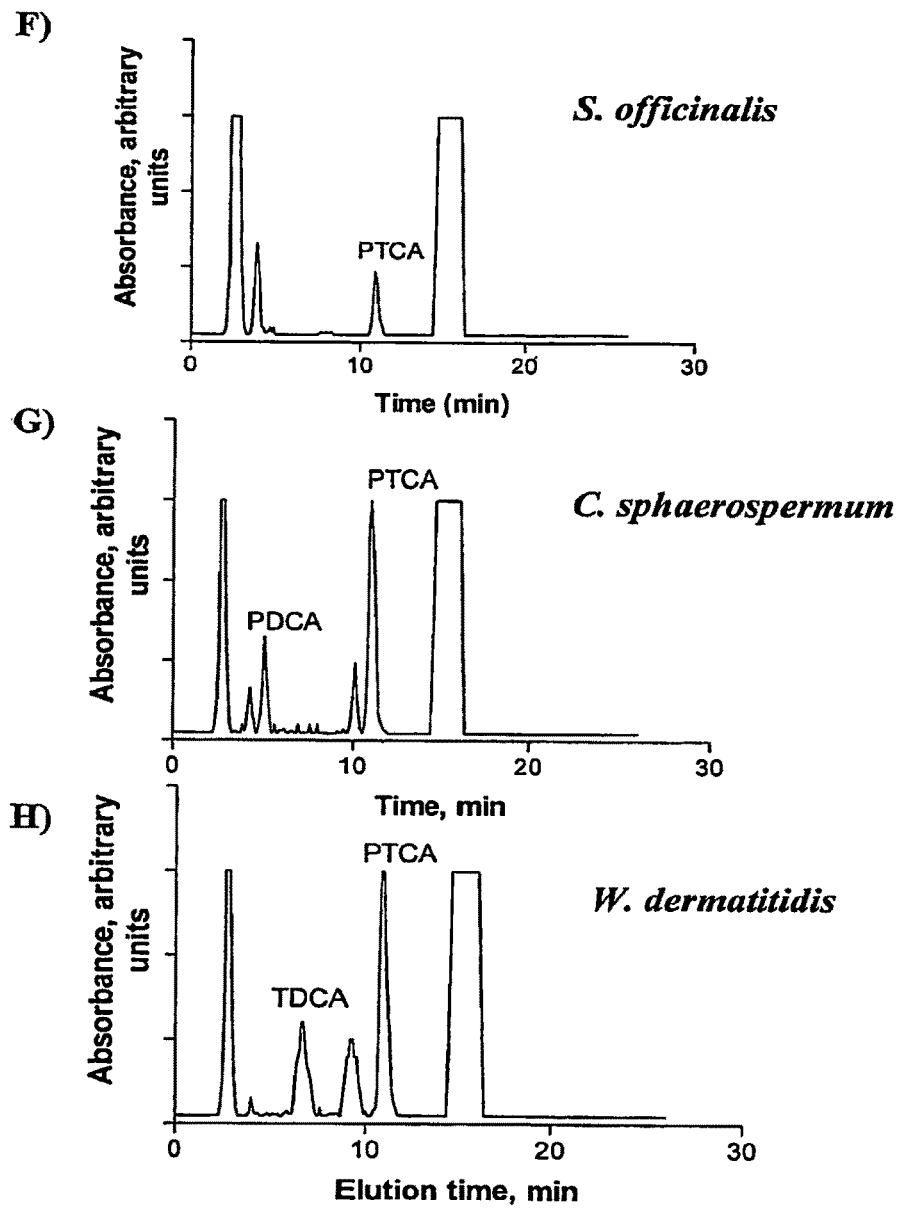
Figure 7A:
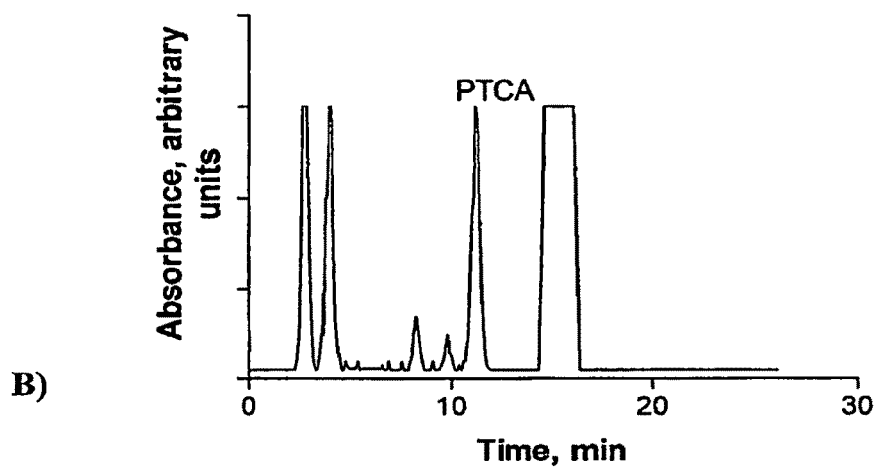
FIG. 7A-7D. HPLC of permanganate-oxidized melanins. A) *C. sphaerospermum* grown on potato dextrose agar; B) *C. sphaerospermum* grown on Sabaroud dextrose agar; C) *C. sphaerospermum* grown on water agar with casein; D) *C. sphaerospermum* grown on water agar with dextrose. PDCA—pyrrole-2,3-dicarboxylic acid; PTCA—pyrrole-2,3,5-tricarboxylic acid; TTCA—1,3-thiazole-2,4,5-tricarboxylic acid; TDCA—1,3-thiazole-4,5-dicarboxylic acid. Absorption was monitored at 255 nm and displayed on the linear scale. Cs—*C. sphaerospermum*.
Figure 7B:
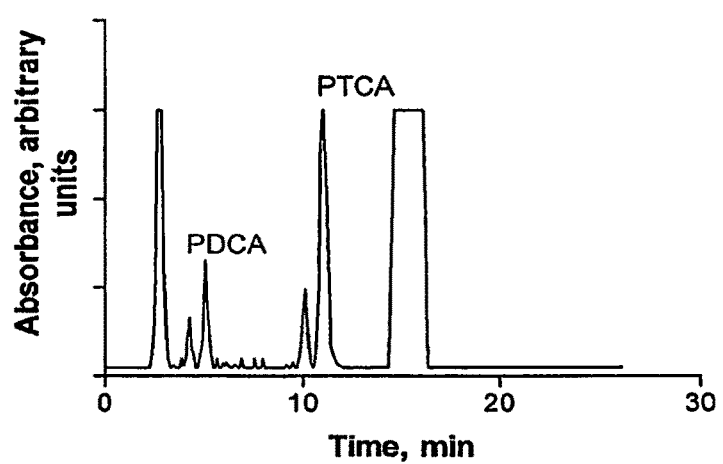
Figure 7C:
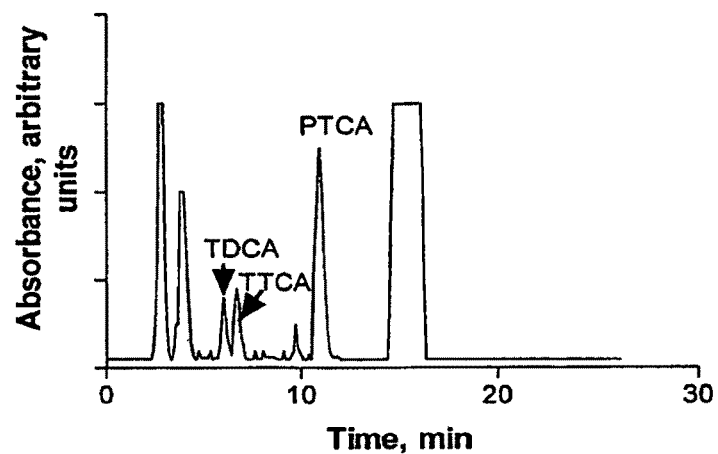
Figure 7D:
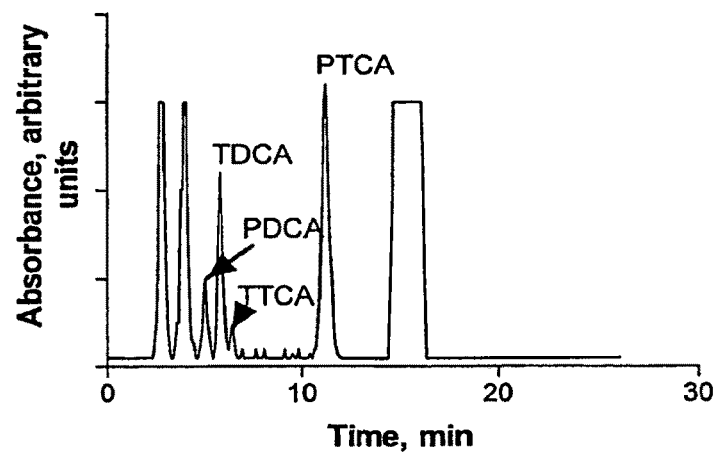
Figures 8A, 8B, 8C:
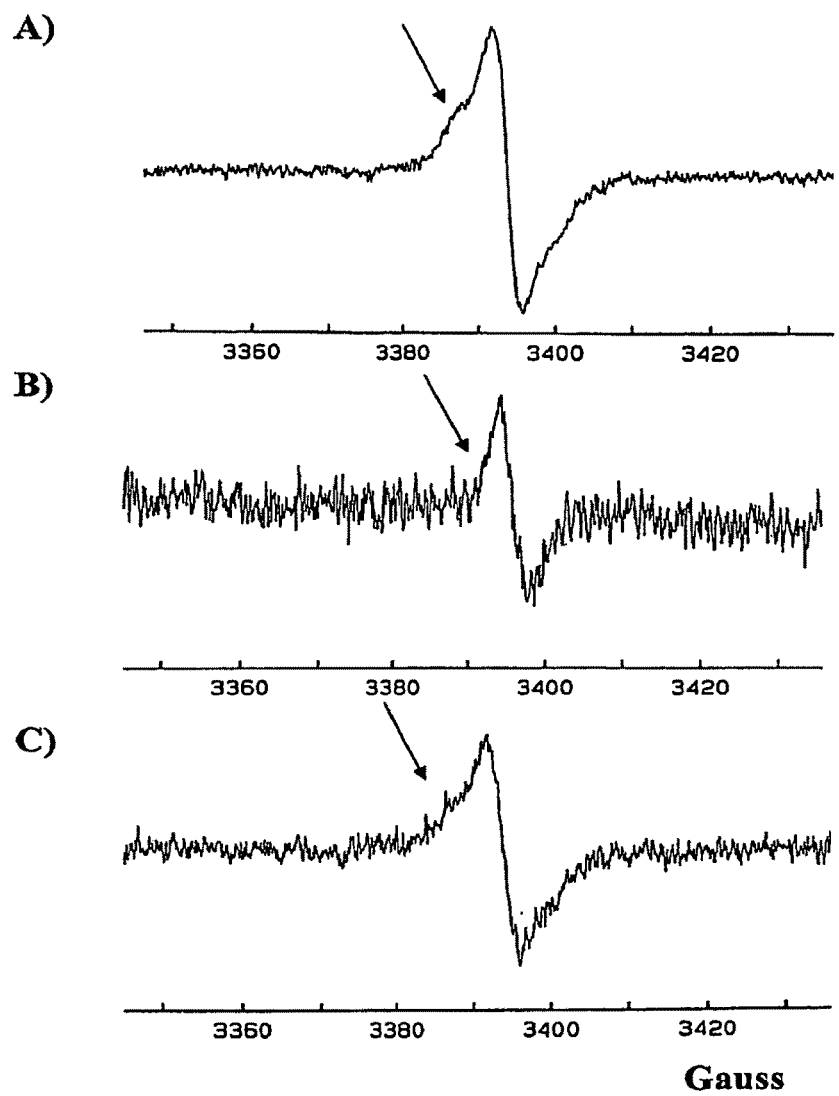
FIG. 8A-8C. ESR spectra. A) *C. sphaerospermum* grown on potato dextrose agar; B) *C. sphaerospermum* grown on Sabaroud dextrose agar; C) *C. sphaerospermum* grown on potato dextrose agar impregnated with 25 µg/mL tricyclazole. Differences in *C. sphaerospermum* ESR spectra in comparison with *C. neoformans* are marked with arrows. ESR spectra were obtained by suspending "ghosts" in water. Ordinate is the derivative of the ESR absorption in arbitrary units. Cs—*C. sphaerospermum*.

The structures of both synthetic [19] and natural melanins including fungal melanin are poorly understood. These pigments are amorphous and insoluble, which preclude a structural solution of melanins given the currently available analytical tools. There are two major types of melanin: eumelanin and pheomelanin. Eumelanin is a dark-brown to black pigment composed of 5,6-dihydroxyindole (DHI) and 5,6-dihydroxyindole-2-carboxylic acid (DHICA) monomer units with 6-9% nitrogen and 0-1% sulfur [20, 21] (FIG. 6A). In contrast, pheomelanin is a reddish-brown pigment composed of benzothiazine monomer units with 8-11% nitrogen and 9-12% sulfur [20, 21] (FIG. 6B). When subjected to acidic permanganate oxidation, DHI converts into pyrrole-2,3-dicarboxylic acid (PDCA) and DHICA into pyrrole-2,3,5-tricarboxylic acid (PTCA), and pheomelanin oxidation results in 1,3-thiazole-2,4,5-tricarboxylic acid (TTCA) and 1,3-thiazole-4,5-dicarboxylic acid (TDCA) [20, 21]. High-pressure liquid chromatography (HPLC) has recently been applied for analysis of *C. neoformans* melanin [22, 23] as well as for *A. fumigatus* and synthetic DHN melanins (unpublished observations). The HPLC analysis of oxidized *C. neoformans* and *H. capsulatum* melanins revealed PTCA and TDCA (FIG. 6D-6E) while only PTCA was detected in the *S. officinalis* chromatogram (FIG. 6F), which was confirmed by matrix assisted laser desorption/ionization time of flight mass spectrometry (MALDI-TOF) of these peaks. Importantly, the chromatographic data revealed a PTCA to TDCA ratio of 0.90 for *H. capsulatum* melanin and 47.7 for *C. neoformans* melanin. Although these ratios are not quantitative measures of eumelanin and pheomelanin in the cells, they indicate that benzothiazine subunits predominate in *H. capsulatum* melanin while DHICA subunits predominate in *C. neoformans* melanin. These results are important for understanding the radioprotective and energy transduction properties of melanin. The number of electrons per gram is an important contributor to the attenuation properties of a material at the energy levels where the Compton effect predominates [14]. Thus, the existence of structures composed of electron-rich covalently linked aromatic motifs could explain radiation scattering properties of melanins and the higher number of electrons in oligomers of pheomelanin relative to eumelanin—388 versus 287—better scattering properties of *H. capsulatum* melanin. Also, pheomelanin contains divalent sulfur (FIG. 6B), which may also contribute to superior radioprotective properties of *H. capsulatum* melanin, as compounds containing divalent sulfur are efficient radioprotectors [24]. Melanins produced by *C. sphaerospermum* (FIG. 6G and FIG. 7) and by *W. dermatitidis* (FIG. 6H) were chemically more diverse than *H. capsulatum* or *C. neoformans* melanins revealing also the peaks assigned to PDCA and peaks at 9-10 min which may be attributed to the oxidized DHN. Analyses by electron spin resonance spectroscopy (ESR) revealed the presence of free radical population (FIGS. 8 and 10C-10F) in all fungi used. Such stable free radical population is considered to be one of melanin's distinguished characteristics [25].

Figure 9:
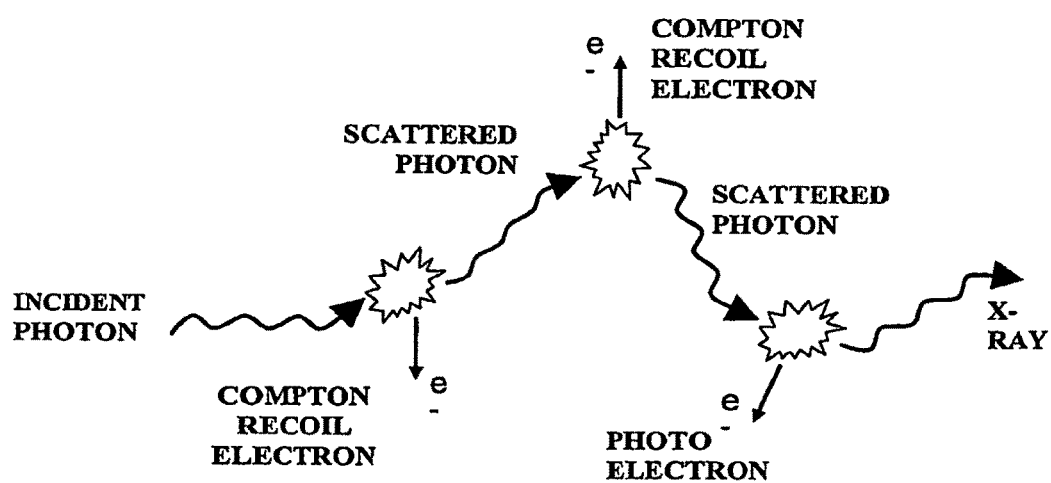
FIG. 9. Diagram illustrating multiple interactions of a photon passing through matter. Energy is transferred to electrons in a sequence of photon-energy degrading interactions (adapted from ref. 14).
Figures 10A, 10B:
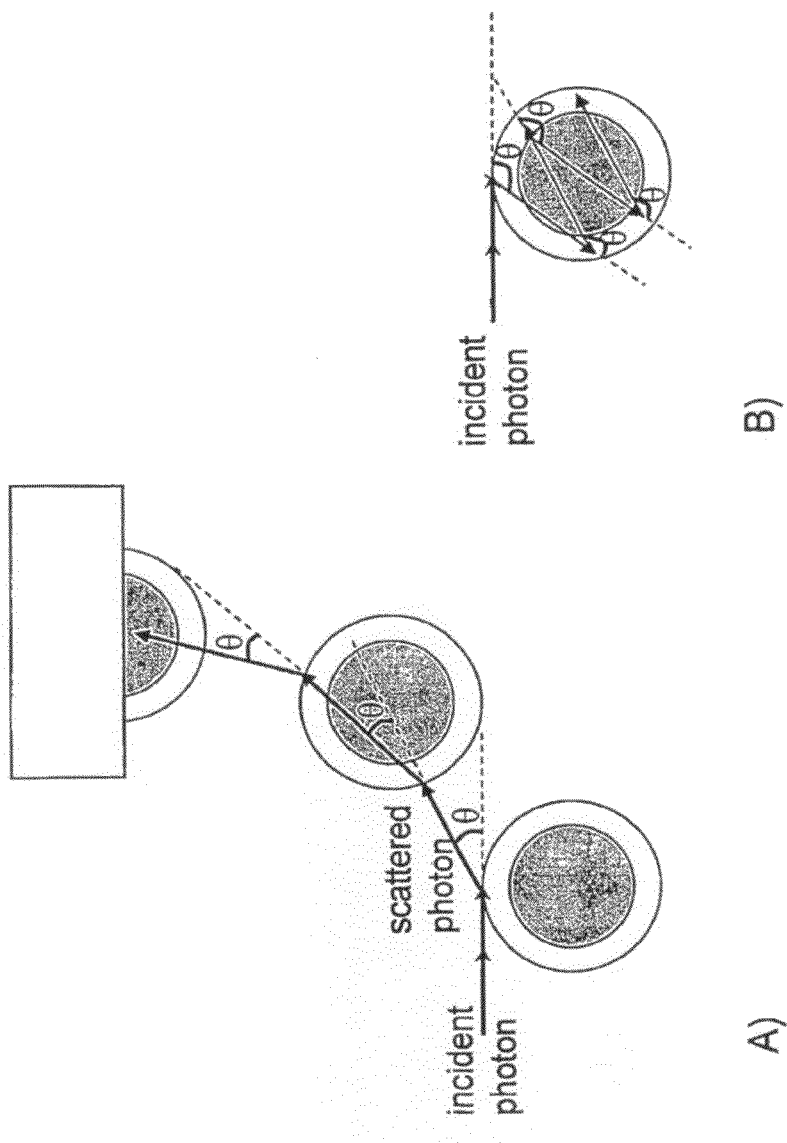
FIG. 10A-10G. Factors contributing to scatter and absorption of ionizing radiation and energy transduction by melanin nanospheres. A) Initial scatter of 662 keV photons when forward scatter predominates; B) oscillation of scattered photons with energies below 300 keV within melanin nanospheres when both forward and backward scatter takes place. ESR spectra: C)*H. capsulatum*; D) *C. neoformans* in dry state; E) *W. dermatitidis* isolate 8656; F) *C. neoformans* after irradiation with 0.3 kGy dose in dry state and subsequent suspension in water. G) Hypothetical electron energy transfer in melanin. ESR spectra in C) were obtained by suspending "ghosts" in water. Ordinate in C-F is the derivative of the ESR absorption in arbitrary units.
Figure 10C:
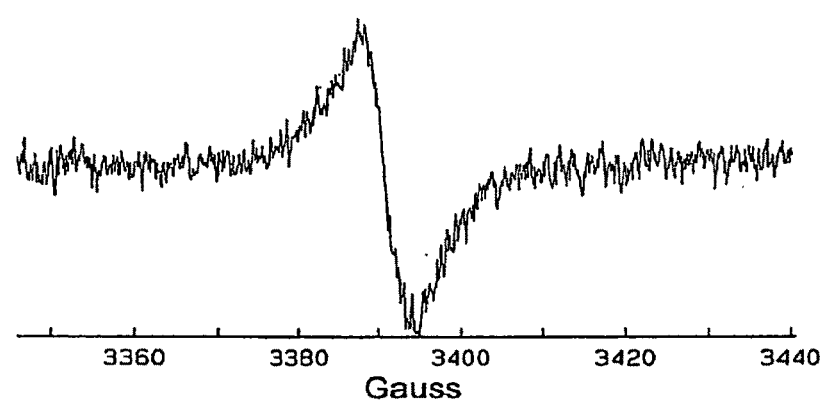

While the scattering of non-ionizing electromagnetic radiation by melanin nanospheres can be described by application of algorithms for calculation of scattering coefficients for a multilayered sphere [26], the interaction of ionizing radiation in the form of high-energy photons with melanin occurs presumably through the photoelectric effect, Compton effect or pair production, depending on the photon energy. For chemical elements with low atomic numbers such as C, N, O and S, which constitute melanin and for 662 keV high-energy photons emitted by the 137-Cs source used in the present experiments, Compton scattering predominates [14]. In Compton scattering the transfer of a photon energy to matter occurs via a cascade of interactions, where the energy of the incident photon is transferred to high-energy electrons, and to secondary photons of progressively lower energy (FIG. 9, Equation 4) until photoelectric effect takes place. The energy of the scattered photon is related to the scattering angle θ by considerations of energy and momentum conservation (Equation 5). During the first scattering events, when the energy of scattered photons is still high, a photon can be expected to pass through a melanin sphere with forward scattering predominating (FIG. 10A). However, when the energy of scattered photons falls below ~300 keV and the probability of backward scattering increases [14], one can speculate that the scattered photons could oscillate within a melanin sphere (FIG. 10B) as the wavelength of gamma photons ($10^{-12}$-$10^{-11}$ m) is $10^5$-$10^6$ times smaller than the diameter of a melanin sphere ($10^{-5}$ m, FIG. 1B). Since the absorbance of radiation by matter also depends on the geometric arrangement of the photon source and the absorber, the assembly of melanin into nanospheres may account for more efficient protection of cells by nanospheres than by powdered melanin. In this regard, when the emission properties of eumelanin were studied post exposure to UV-A radiation, the observed rapid and non-exponential depolarization dynamics was found to be due to energy transfer processes within spherical granules of eumelanin [27].

The high-energy electrons generated by Compton scattering are ultimately responsible for the radiobiologic effects caused by gamma radiation by either direct interactions with DNA or through radiolysis of water in the cells, a process that results in the formation of reactive short-lived free radicals capable of damaging DNA. Melanin may trap these high-energy electrons and prevent them from entering a cell, thus performing its function as a radioprotector. The electrons may then undergo secondary interactions with melanin molecules with their energy gradually transferred to melanin.

Figure 10D:
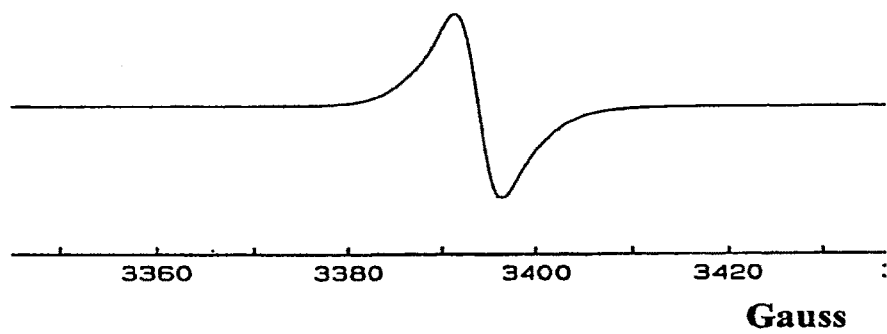
Figure 10E:
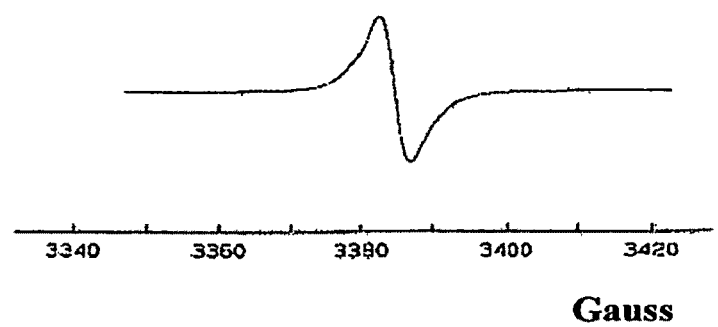
Figure 10F:
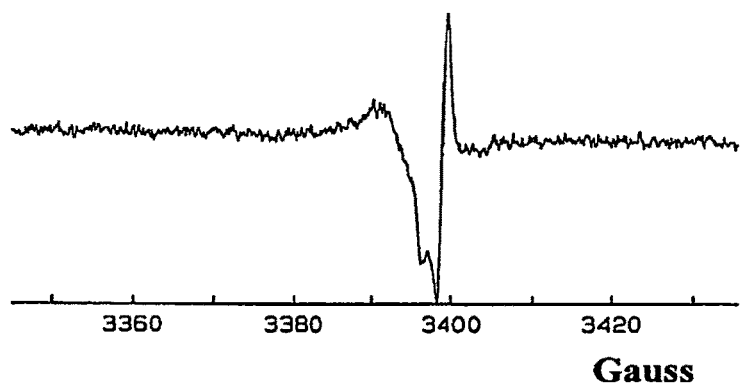
Figure 10G:
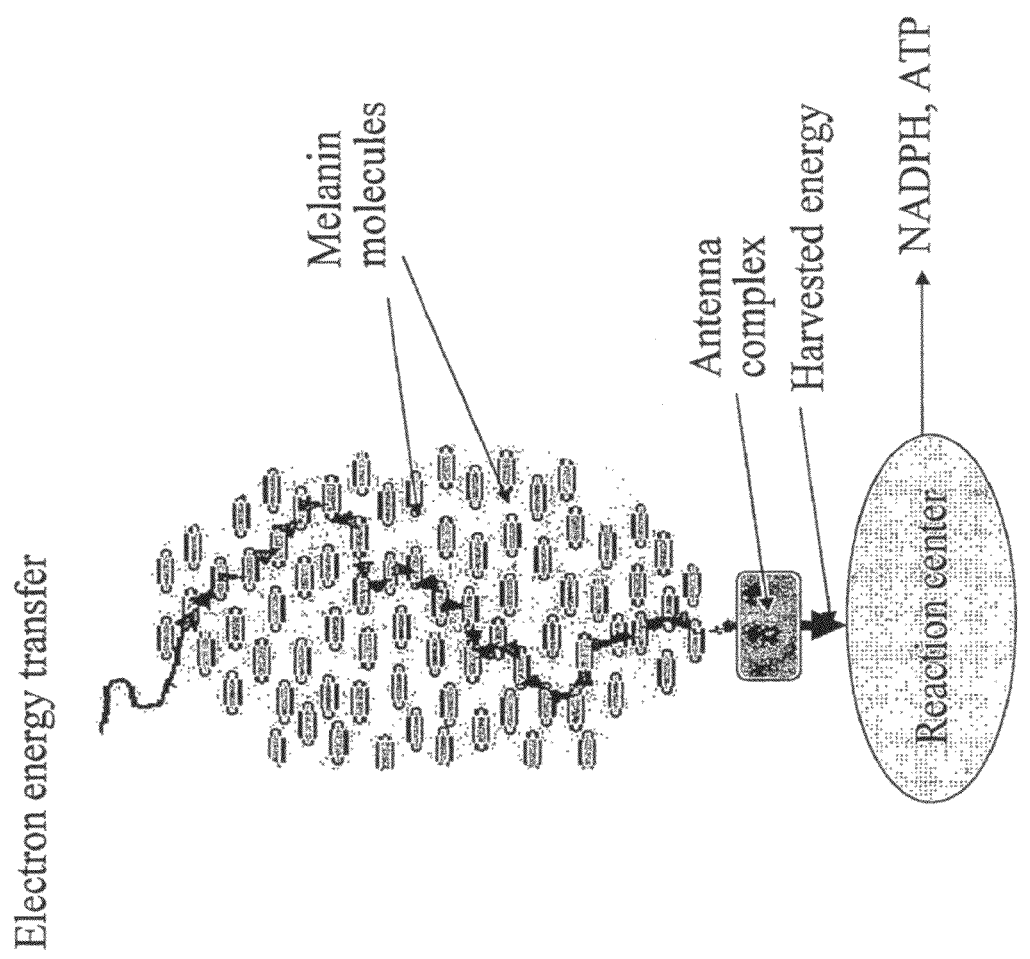

One important indication of melanin participation in energy transduction process was the dramatic change in ESR signal of *C. neoformans* dry melanin "ghosts" after these "ghosts" were subjected to 0.3 kGy irradiation and suspended in water (FIGS. 10D and 10F). The drastic change in the ESR spectra of irradiated with gamma photons melanin in comparison with the untreated sample (FIGS. 10 F and 10 D, respectively), combined with the increased ability of irradiated melanin to increase the velocity of NADH-ferricyanide reaction (Table 2), can be explained by the ability of melanin to store energy in the form of absorbed Compton electrons and then gradually release it.

To prove unambiguously that subjecting melanin to ionizing radiation increases its electron transfer properties, dry *C. neoformans* melanin was irradiated for 20 and 40 min with 137-Cs source and its electron transfer properties were investigated in the coupled oxidation of NADH and reduction of ferricyanide. It is known that melanin is acting as an electron-transfer agent in this system [28]. Irradiation of melanin for 20 min increased the velocity of NADH/ferricyanide coupled reaction 3-fold in comparison with non-irradiated melanin, while 40 min irradiation has even more profound effect causing 4-fold increase in velocity (Table 2).

TABLE 2

NADH-ferricyanide-melanin reaction in presence of untreated and irradiated C. neoformans melanin.

| | Reaction system | | |
|---|---|---|---|
| | Ferricyanide + melanin | Ferricyanide + NADH + melanin | |
| Sample | Ferricyanide reduced | NADH oxidized | Ferricyanide reduced |
| untreated melanin | 40 nmol<br>V = 9 nmol/min | 37 nmol | 75 nmol<br>V = 30 nmol/min |
| irradiated melanin, 20 min | 60 nmol<br>V = 13 nmol/min | 100 nmol | 200 nmol<br>V = 80 nmol/min |
| irradiated melanin, 40 min | 170 nmol<br>V = 38 nmol/min | 150 nmol | 300 nmol<br>V = 120 nmol/min |

V - initial velocity is expressed in nanomoles of ferricyanide reduced per min.

The influence of other, non-ionizing forms of radiation across the electromagnetic spectrum—heat (infrared radiation), visible light and UV light—was investigated on the electron-transfer properties of melanin in NADH/ferricyanide coupled reaction. All these forms of radiation increased the ability of melanin to transfer electrons (Table 3). 50 μg of C. neoformans melanin was used in the reactions. Melanin was subjected to 40 min treatment, placed into dry ice following treatments and taken up in the ferricyanide solution immediately before measurements. To exclude contribution of heat component during irradiation of melanin with 250 W light, the samples were placed in 25° C. water bath.

TABLE 3

Increase in electron-transfer properties of melanin in NADH/ferricyanide coupled reaction after exposure to different forms of electromagnetic radiation.

| Radiation type | Photon energy eV | Increase in initial velocity in NADH/ferricyanide reaction |
|---|---|---|
| Ionizing radiation from 137-Cs source | 661,000 | 4.0 |
| UV, 254 nm | 4.7 | 3.9 |
| Visible light 250 W | 3 | 4.0 |
| Heat, 75° C. | 0.1 | 3.7 |
| photosynthesis | 3 | N/A |

Growing melanized and non-melanized cells at room temperature and 30° C. demonstrated increased metabolism in melanized cells at both room temperature and 30° C. in comparison with non-melanized controls (Table 4). One can speculate by analogy with photosynthesis that in melanized cells the energy of ionizing radiation is harvested by an antenna complex and funneled to the reaction center where this energy is used to split water molecules. Splitting of water molecules starts a flow of electrons, which are used to reduce $NAD^+$ to NADH ("portable electrons") and convert ADP by addition of phosphate into ATP ("portable energy") (FIG. 10G) in a process termed herein as "radiosynthesis". The process of energy transduction and radiosynthesis is likely to be confined in fungi to the cell wall where melanin is localized.

TABLE 4

Metabolic activity of melanized and non-melanized C. neoformans cells at different temperature as determined by XTT assay.

| | Absorbance in XTT assay | | |
|---|---|---|---|
| Temperature, ° C. | Melanized | Non-melanized | Melanized/Non-melanized |
| 22 | 2.7328 | 1.3906 | 1.95 |
| 30 | 2.8446 | 1.3282 | 2.14 |

Figure 11A:
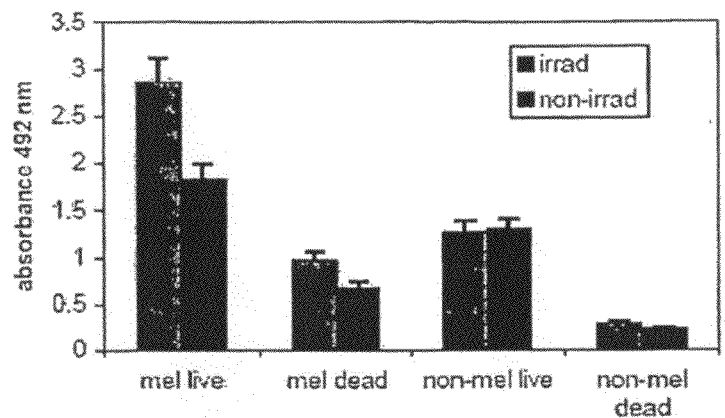
FIG. 11A-11C. The influence of ionizing radiation or heat on the metabolic activity of melanized and non-melanized *C. neoformans* cells. A, B) irradiated and non-irradiated cells: A) XTT; B) MTT. C) XTT of cells grown at room temperature (22° C.) or at 30° C. The cells were kept in the dark while being exposed to ionizing radiation or different temperatures. Following the exposure, XTT or MTT reagents were added to the samples and absorbance was measured at 492 or 550 nm for XTT and MTT, respectively.
Figure 11B:
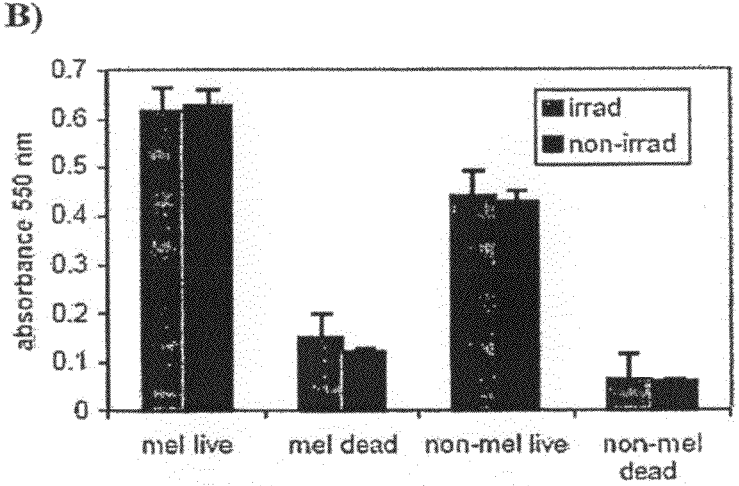

Melanized and non-melanized C. neoformans cells showed increased metabolic activity following exposure to ionizing radiation or heat. It was investigated whether the changes in electron transfer properties of melanin after exposure to ionizing radiation influence cellular metabolic activity. The metabolic activity of C. neoformans cells was evaluated with 2,3-bis(2-methoxy-4-nitro-5-sulfophenyl)-5-[(phenylamino) carbonyl]-2H-tetrazolium hydroxide (XTT assay) [52] and 2-(4,5-dimethyl-2-thiazolyl)-3,5-diphenyl-2H-tetrazolium bromide (MTT assay). The use of XTT and MET assays in parallel can help to deduce the location of the melanin-mediated electron transfer in the cells since positively charged MTT is taken into the cells via the plasma membrane potential and is reduced intracellularly; while the negatively charged XTT is largely cell-impermeable and its reduction occurs extracellularly, at the cell surface [53]. The melanized and non-melanized C. neoformans cells were exposed to ionizing radiation in the dark at 30° C. overnight. The irradiation was performed in a constant radiation field of 0.05 mGy/hr, a non-fungicidal dose that is comparable to the radiation flux inside the Chernobyl reactor. Following exposure to radiation, the XTT or MTT reagents were added to the samples and absorbance was measured at 492 or 550 nm, respectively. The XTT assay showed significantly increased metabolic activity in the irradiated melanized cells in comparison with non-irradiated melanized or irradiated non-melanized cells (FIG. 11A). Increased absorbance at 492 nm was also observed for dead (heat killed) melanized cells in comparison to non-melanized ones, showing that melanin by itself is capable to reduce XTT reagent (FIG. 11A). Irradiation of dead cells caused significant increase in the XTT reduction thus confirming that radiation enhances electron-transfer properties of melanin. In contrast, there was no difference between the irradiated and non-irradiated melanized and non-melanized cells subjected to MTT assay (FIG. 11B). The difference between the MTT and XTT assays may be explained by the occurrence of radiation-related, melanin-mediated electron transfer events near the cell wall where melanin is located that led to higher XTT reduction in irradiated melanized samples. Hence, the MTT/XTT results localized the increased metabolic activity following irradiation to the extracellular compartment where the melanin pigment is found. Interestingly, both irradiated and non-irradiated melanized cells showed higher metabolic activity by MIT assay than non-melanized cells, suggesting a higher metabolism for the melanized state (FIGS. 11A,B). Given that melanization is associated with reduced pore size that could reduce passive nutrient uptake [12] and that melanin is synthesized from highly reactive cytotoxic intermediates of the oxidation of L-Dopa, it is possible that melanization requires a higher metabolism for cell survival.

Figure 11C:
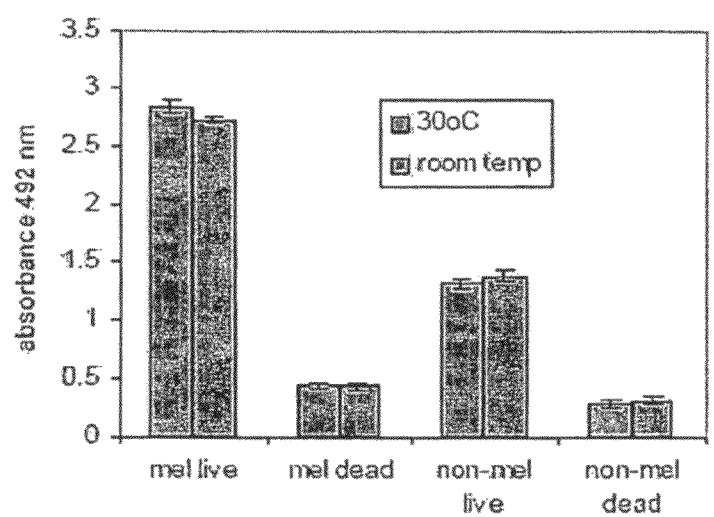

In another series of experiments, the melanized and non-melanized cells were grown overnight in the dark at room temperature (22° C.) or 30° C. Melanized cells demonstrated increased metabolism at both temperatures in comparison with non-melanized controls (FIG. 11C), and increasing the temperature to 30° C. caused statistically significant increase in metabolic activity of melanized cells (P<0.05) while a small decrease was observed for non-melanized cells. Overall, these experiments showed that the increase in electron transfer properties of melanin post exposure to ionizing radiation and possibly heat influences the metabolic activity of the melanized cells.

Ionizing radiation enhances growth and $^{14}$C-acetate uptake of melanized *C. neoformans* cells. To expand the observations of the influence of irradiated melanin on the metabolism of melanized cells, measurement was made of the growth of melanized and non-melanized *C. neoformans* cells supplied with limited nutrients and placed into the radiation flux. To maintain a steady population of melanized cells, the same H99 strain of *C. neoformans* was used as in metabolism experiments since it is capable of making melanin when maintained with L-Dopa while its laccase disrupted [Lac(−)] mutant is incapable of melanization [54]. The cells were grown into stationary phase up to 30 hr. There were significantly more (P=0.006) CFUs for irradiated melanized wild type H99 samples at 18, 23 and 30 hr than for non-irradiated samples (FIG. 12B), while the difference in CFUs at 18 hr between irradiated and non-irradiated Lac(−) mutant was not significant (FIG. 12C).

Figure 12A:
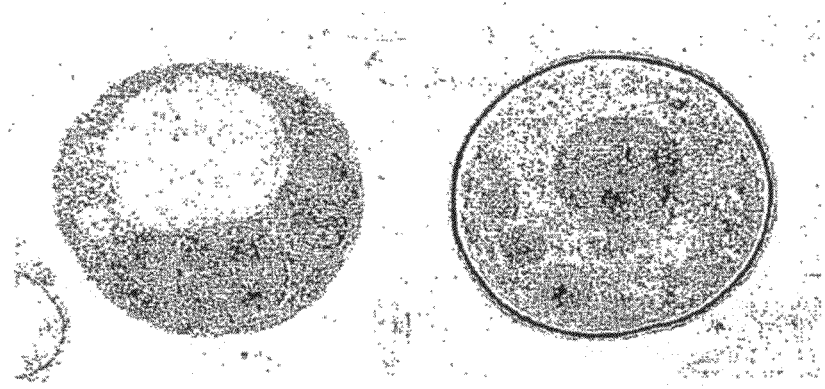
FIG. 12A-12D. Growth of melanized *C. neoformans* H99 cells and non-melanized Lac(−) H99 cells lacking the laccase enzyme under conditions of limited nutrients supply in a radiation field of 0.05 mGy/hr or at background radiation level. A) TEM image of non-melanized (left) and melanized *C. neoformans* cells (right); B) melanized H99 cells; C) non-melanized Lac(−) H99 cells; D) light microscopy image of irradiated wild type H99 depicting a mixed population of mature cells with large capsules and young cells with small capsules. TEM original magnification—×13,000; light microscopy—×400.
Figure 12B:
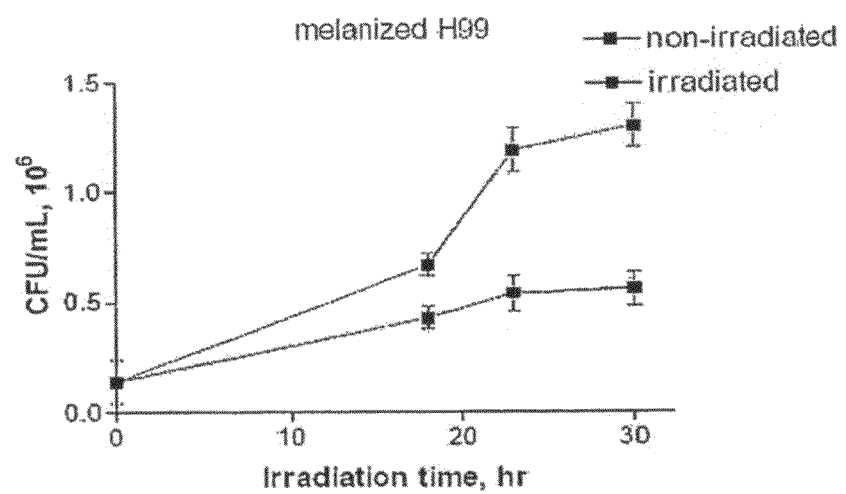
Figure 12C:
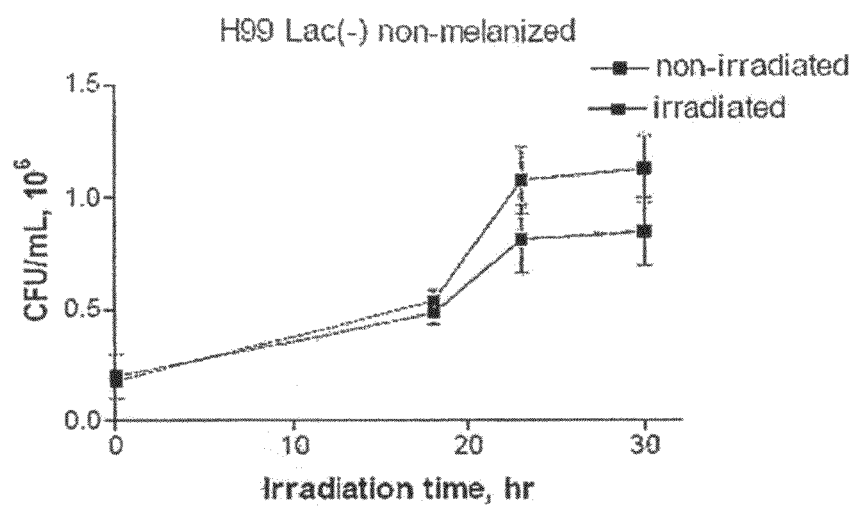
Figure 12D:
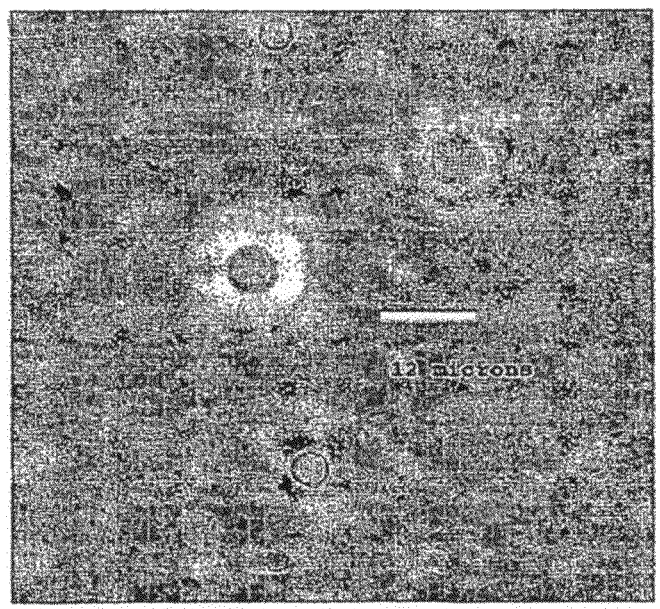
Figure 13A:
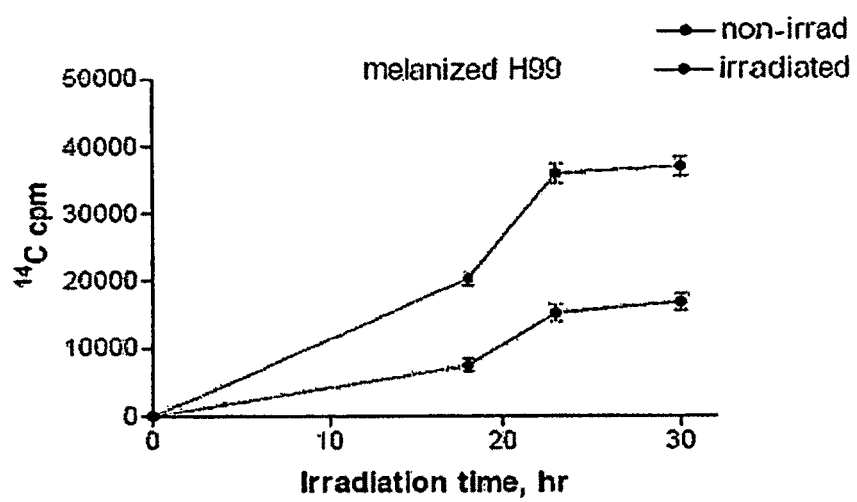
FIG. 13A-13C. Incorporation of $^{14}$C-acetate into melanized and non-melanized *C. neoformans* cells. Melanized *C. neoformans* H99 cells and non-melanized Lac(−) H99 cells lacking laccase enzyme were grown under conditions of limited nutrients supply in radiation field of 0.05 mGy/hr or at background radiation level. A) melanized H99 cells; B) non-melanized Lac(−) H99 cells; C) irradiated to non-irradiated cells CPUs and cpms ratios (normalized CFUs and cpms) for melanized H99 and non-melanized Lac(−) H99 cell.
Figure 13B:
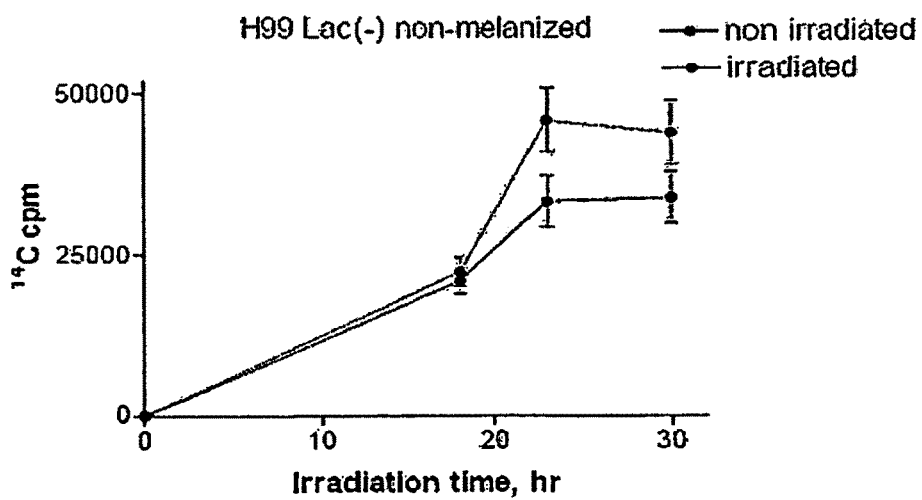
Figure 13C:
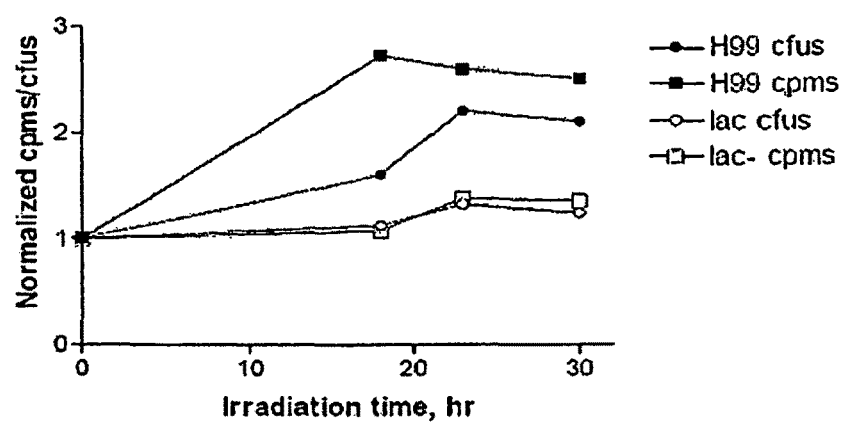

Lac(−) without radiation in the presence of L-dopa grows better than wild type H99 (FIGS. 12B and C). Although the basis for this difference is not understood, it may be related to melanin limited porosity in the wild type melanized strain, since pore size decreases with culture age [12] and might reduce the availability of nutrients. Also, the process of melanization involves an oxidation reaction with generation of toxic intermediates, which may impose a certain metabolic cost that could translate into slower in growth relative to Lac(−) cells. The slight increase in the CFU's of irradiated Lac(−) cells at 23 and 30 hr is probably due to the well documented phenomenon that very low doses of ionizing radiation can stimulate cell proliferation [17, 18]. However, the crucial difference between the wild type H99 and Lac(−) cells is that the exposure to ionizing radiation produced approximately 2.5-times more CFUs in irradiated melanized cells than in non-irradiated melanized controls, while irradiation of Lac(−) cells resulted only in a 1.1 increase in CFUs (FIG. 13C). The dry weight measurements performed at 20 hr showed a consistent and significant 6.5% increase for irradiated melanized samples (P=0.02) while there was no difference in weight for the mutant strain after irradiation. The relatively small yet significant increase in dry weight of the melanized cells is a result of the high percentage of immature cells, with smaller capsules synthesized de novo in the dividing melanized irradiated cell culture (FIG. 12D). In this regard, a cell diameter that is one-half to one-third of that for a mature cell results in a 8- and 26-fold decrease in cell mass, respectively. Quantification of whole cell sizes using India ink stained cells showed that proximately 50% of melanized irradiated cells had volumes 2 times smaller (FIG. 12D) than those in the irradiated Lac(−) mutant population, accounting for the relatively small increase in the dry weight of the melanized H99 samples in comparison to their larger increase in CFUs.

To obtain additional evidence that exposure to ionizing radiation enhances melanized cell growth, measurement was made of the incorporation of a $^{14}$C-labeled carbon source (acetate) into melanized and non-melanized *C. neoformans* cells with and without radiation flux. In the photosynthesis field the incorporation of $^{14}$C-acetate in bacteria subjected to visible light is an assay considered to be indicative of their photoheterotrophic capabilities [55]. A lower absolute uptake of $^{14}$C-acetate by wild type H99 was measured compared to Lac(−) cells (FIGS. 13A,B). This difference in absolute $^{14}$C-acetate uptake may reflect relative differences in cell wall porosity and/or in the well-known radiation induced growth spurt, since melanized cells would receive less cytoplasmic radiation given that the pigment is an effective radioprotector [8, 9]. There was no incorporation of $^{14}$C-acetate into heat killed melanized or non-melanized cells, which excludes the possibility that radiation promoted the passive absorption of $^{14}$C-acetate on melanin. Importantly, when melanized and non-melanized Lac(−) H99 cells were incubated with $^{14}$C-acetate with and without radiation, there was almost 3 times more incorporation of $^{14}$C-acetate into irradiated melanized cells than into non-irradiated melanized cells, while the ratio of $^{14}$C-acetate incorporation into irradiated to non-irradiated Lac(−) cells was only slightly higher than 1 (FIGS. 13A,B,C). Overall, these results demonstrate that the presence of melanin contributes to the enhancement of cellular growth upon exposure to ionizing radiation in conditions of limited nutrients.

Discussion

Melanins are unique biopolymers that protect living organisms against UV and ionizing radiation, and extreme temperatures. Melaminogenesis can be viewed as a complex adaptation of living organisms to difficult conditions when sources of energy and nutrients are scarce. The question of melanin function in microorganisms is even more intriguing when considered from a paleobiological perspective. Highly melanized fungi spores occur in great amounts in the layers of the beginning Cretaceous period when many species of animals and plants died out. This period coincides with the Earth's crossing the "magnetic zero," and thus losing its "shield" against cosmic radiation [29]. Others have hypothesized that that radiation from a putative passing star called Nemesis contributed to the extinction events [30]. Melanin is also a virulence factor for fungi, which have been recently proposed to have contributed to the extinctions at the end of Cretaceous [31]. Hence, melanins are ancient pigments that have probably been selected because they enhance the survival of melanized fungi in both the environment and in various hosts. The emergence of melanin as a non-specific protective material may be a result of the relative ease with which these complicated aromatic structures can be synthesized from a great variety of precursors [2, 4, 5, 10, 15, 16, 19-23].

The electronic complexity of melanins allows them to scatter/trap photons and electrons, which could allow melanin to perform the dual function in microorganisms of radioprotector and energy transducer. The present results strongly suggest that fungal melanin-mediated radioprotection of living cells results from a combination of Compton scattering by the high number of electrons in its macromolecules, energy attenuation of photons as a consequence of high angular scattering caused by the geometry of spheres, and free electron and radical quenching.

The ability of melanized fungi to utilize the energy of ionizing radiation in its metabolism is implied by three observations made in this study: 1) melanized wild type and complemented with wild type gene *W. dermatitidis* cells exposed to levels of radiation approximately 500 higher than background grew significantly faster as indicated by the presence of more cells than non-irradiated melanized, complemented or irradiated albino controls; 2) melanin dramatically changed its electronic structure post-radiation exposure as shown by amplitude changes in the ESR signal; and 3) electron transfer properties of melanin in the NADH oxidation/ reduction reaction increased 4-fold after melanin irradiation. Indirect evidence consistent with the present finding that melanin can serve as a transducer of radioactive energy can be found in two published observations: 1) the melanotic fungus *C. cladosporioides* manifests the phenomenon of radiotropism such that it grows in the direction of radioactive particles and is widely distributed in the areas surrounding the site of Chernobyl nuclear accident in 1986 [7]; and 2) the phenomenon of "photosynthesis without light" has been recently reported to take place in the geothermally illuminated environment on the bottom of the ocean [32], thus establishing the precedent that certain life forms can utilize unusual forms of energy.

It is possible that "radiosynthesis" played an important role during the early stages of life on Earth and that melanized fungi were able to function as autotrophs—organisms capable of making their own food. Given that terrestrial life can capture visible electromagnetic radiation by photosynthesis, infrared radiation from geothermal ocean vents [32] and chemical energy from minerals, it is not surprising that some organisms can also harness high energy photons by capturing them with melanin-type pigments. Radiosynthesis provides the possibility of utilizing ionizing radiation as an energy source for the sustenance of life.

Prophetic Applications

Production of food sources. The growth of organisms such as microorganisms, mushrooms and plants will be increased by increasing the melanin content of the microorganism, mushroom or plant and exposing the melanized microorganism, mushroom or plant to radiation, such as ionizing radiation. These food sources are expected to be especially important in environments that are low in sunlight and high in radiation, such as outer space. Alternatively, certain useful plants, mushrooms, or microbes may be grown in the presence of radioactive material such as found in radiation waste sites and harness radiation for growth.

Containment of radioactively contaminated sites. Melanin isolated from melanized organisms and/or melanized microorganisms will be used in environmental bioremediation. The following types of radiation are given off by radioactive material: alpha particles, beta particles, x-rays, and gamma rays. The spread of radioactive particles will be reduced by applying the melanized microorganisms or melanin to the radioactive particles. The melanin is expected to encapsulate the radioactive particles and thereby reduce their spread. Thus, for example, the melanized microorganisms or melanin may prevent the spread of radioactive contamination to ground water. Similarly, melanized or melanin-containing microorganisms will be used to contain radiation from radioactive waste and biomedical radioactive materials. Melanin and melanized microorganisms may be used in remediation in connection with, for example, waste containers, fuel cladding, packaging containers, transport coverings for land, air, and water vessels, and nuclear waste clean-up.

Treatment of buildings to reduce entry of radon and radiation from radon. Radon is a gas that forms naturally during the decay of uranium-238. Radon that occurs naturally in soil can seep from the soil into homes and other buildings. Melanin and/or melanin-containing microorganisms and/or melanized microorganisms will be added to paints, coatings and/or building materials. Melanin-based paints and coatings applied to the foundations of buildings and areas where pipes enter the buildings, and melanin-based materials in the foundation of the building can be used for the purpose of trapping radon when it is emitted from rocks or soil before radon enters the building. Radon decays over the course of several days to 210-Pb, which is a beta and gamma emitter and has a half-life of 22 years. Melanin should absorb 210-Pb even tighter than radon through chemisorption as melanin is known to bind two-valent metals and thus should reduce the entry not only of radon but also of radioactive lead into the environment of the building. The melanin can comprise synthetic melanin and/or melanin isolated or derived from a biological source, such as a plant, an animal, a microorganism, and/or a melanin-containing cell, or generated by chemical synthetic process. Suitable animals include, but are not limited to, helminthes, cuttlefish and squids. The microorganism can be, e.g., a bacterium or preferably a fungus. Suitable fungi include, but are not limited to, *Cryptococcus neoformans* and/or *Histoplasma capsulatum*. The melanin can be from an organism that normally contains melanin. The melanin can be from a melanized organism. The melanin can comprise, for example, polymerized L-dopa, epinephrine, methyldopa, a substituted phenol derivative and/or a phenolic derivative that polymerizes into melanin, allomelanin, pheomelanin and/or eumelanin. Eumelanins are derived from the precursor tyrosine. Pheomelanin is derived from the precursors tyrosine and cysteine. Allomelanins are formed from nitrogen-free precursors such as catechol and 1,8-dihydroxynaphthalenes. The melanin can comprise pheomelanin and eumelanin, wherein the ratio of pheomelanin to eumelanin is at least 1:1. Preferably, the melanin contains divalent sulphur. The melanin can be in the form of melanin nanoshells, for example, nanospheres, nanotubes, nanoellipsoids, nanorods, nanoballs, or other suitable shape. The nanoshells can be hollow or filled with the same type of melanin as used in the shell or with a different type of melanin or with another material. The nanoshell can have a thickness of about 10 nm to about 1,000 nm. In one embodiment, the nanoshell has a thickness of about 100 nm.

Promotion of gene expression If certain genes are found to be expressed at elevated levels in melanized organisms under the influence of radiation, the regulatory portions of these genes can be used to promote expression of desirable genes, including, but not limited to, genes encoding enzymes for assimilation of radioactive compounds and genes encoding useful products such as starch.

Energy transduction by melanin (e.g., solar to electrical and/or heat). Melanin can function as an energy transducer. It is envisioned that melanins can capture electromagnetic radiation and convert that radiation to other forms of energy including electrical and heat energy, for example by using melanin-containing panels for the conversion of solar energy to electric energy and/or heat energy. The complex chemical structure of melanin is envisioned to allow it to capture photons and convert this energy into electrical energy. Such solar panels may be used in homes, vehicles, farms, factories, and ships to both provide electrical and heat energy. Melanin could be used as the energy transducing component for the solar panels. Furthermore, melanin could capture solar radiation, convert it to heat, and transfer the heat to water or air to generate warmth or drive a thermal engine. As such, energy transducers comprising melanin will be provided. The melanin can comprise synthetic melanin and/or melanin isolated or derived from a biological source, such as a plant, an animal, a microorganism, and/or a melanin-containing cell, or generated by chemical synthetic process. Suitable animals include, but are not limited to, helminthes, cuttlefish and squids. The microorganism can be, e.g., a bacterium or preferably a fungus. Suitable fungi include, but are not limited to, *Cryptococcus neoformans* and/or *Histoplasma capsulatum*. The melanin can be from an organism that normally contains melanin. The melanin can be from a melanized organism. Melanin can also be used in the form of melanin-containing microorganisms or melanized microorganisms. The melanin can comprise, for example, polymerized L-dopa, epinephrine, methyldopa, a substituted phenol derivative and/or a phenolic derivative that polymerizes into melanin, allomelanin, pheomelanin and/or eumelanin. Eumelanins are derived from the precursor tyrosine. Pheomelanin is derived from the precursors tyrosine and cysteine. Allomelanins are formed from nitrogen-free precursors such as catechol and 1,8-dihydroxynaphthalenes. The melanin can comprise pheomelanin and eumelanin, wherein the ratio of pheomelanin to eumelanin is at least 1:1. Preferably, the melanin contains divalent sulphur. The melanin can be in the form of melanin nanoshells, for example, nanospheres, nanotubes, nanoellipsoids, nanorods, nanoballs, or other suitable shape. The nanoshells can be hollow or filled with the same type of melanin as used in the shell or with a different type of melanin or with another material. The nanoshell can have a thickness of about 10 nm to about 1,000 nm. In one embodiment, the nanoshell has a thickness of about 100 nm.

Energy storage by melanin. Some melanins have been shown to contain a stable free radical population that can be measured by electron spin resonance [1, 50, 51]. Irradiation of melanin with electromagnetic or particulate radiation can increase the electron spin resonance signal, indicating that melanins can store energy and are thus energy storage pigments. This energy may be released at a later time to provide useful work. Hence it is envisioned that melanins can serve as batteries for storing electrical, electromagnetic and thermal energy. Energy stored in melanins may be released slowly or rapidly. As such, energy storage devices, batteries, and means comprising melanin will be provided. The melanin can comprise synthetic melanin and/or melanin isolated or derived from a biological source, such as a plant, an animal, a microorganism, and/or a melanin-containing cell, or generated by chemical synthetic process. Suitable animals include, but are not limited to, helminthes, cuttlefish and squids. The microorganism can be, e.g., a bacterium or preferably a fungus. Suitable fungi include, but are not limited to, *Cryptococcus neoformans* and/or *Histoplasma capsulatum*. The melanin can be from an organism that normally contains melanin. The melanin can be from a melanized organism. Melanin can also be used in the form of melanin-containing microorganisms or melanized microorganisms. The melanin can comprise, for example, polymerized L-dopa, epinephrine, methyldopa, a substituted phenol derivative and/or a phenolic derivative that polymerizes into melanin, allomelanin, pheomelanin and/or eumelanin. Eumelanins are derived from the precursor tyrosine. Pheomelanin is derived from the precursors tyrosine and cysteine. Allomelanins are formed from nitrogen-free precursors such as catechol and 1,8-dihydroxynaphthalenes. The melanin can comprise pheomelanin and eumelanin, wherein the ratio of pheomelanin to eumelanin is at least 1:1. Preferably, the melanin contains divalent sulphur. The melanin can be in the form of melanin nanoshells, for example, nanospheres, nanotubes, nanoellipsoids, nanorods, nanoballs, or other suitable shape. The nanoshells can be hollow or filled with the same type of melanin as used in the shell or with a different type of melanin or with another material. The nanoshell can have a thickness of about 10 nm to about 1,000 nm. In one embodiment, the nanoshell has a thickness of about 100 nm.

Preparation of Melanin-Containing Plastics: Melanin Isolated from Melanized organisms and/or melanized microorganisms will be used for the preparation of melanin-containing materials such as plastics. To make plastics impregnated with melanin, the melanin will be dispersed in a liquid monomer, such as diethylene glycol bis(allyl-carbonate), otherwise know as CR-39, styrene, or methylmethacrylate. Polymerization of the plastic monomer will be initiated with the help of a free-radical initiator. For example, 400 mg benzoyl peroxide will be dissolved in 10 mL of diethylene glycol bis(allyl-carbonate) (CR-39) at 50° C. Then, melanin will be added, under thorough mixing, in increasing amounts starting from 30 mg until it is possible to form a homogeneous mixture. The mixture will be heated at 50° C. for one day. The mixture will be heated for two additional days at 65° C. under nitrogen, and then cured in a vacuum oven at 110° C. for 2 h.

Incorporation of melanin between two layers of material: Melanin isolated from melanized organisms and/or melanized microorganisms will be used for the preparation of melanin-containing materials. Melanin will be added to a binder/adhesive in the form of a suspension to achieve dispersion of melanin in the binder/adhesive. Then, a hardener will be combined with the binder/adhesive, which will then be immediately "sandwiched" between two layers of material. For example, increasing amounts of purified melanin starting from 500 mg will be suspended in 10 mL of chloroform. This suspension will be mixed with 2 mL epoxy resin. The chloroform will then be removed by evaporation leaving melanin homogeneously dispersed in the epoxy resin. Epoxy catalyst, or hardener, will be added, and the mixture will be slowly stirred. Drops of the product will be deposited onto a material such as a plastic or glass, and an identical material will be placed on top of the melanin-epoxy suspension.

Coating surfaces with melanin: Melanin isolated from melanized organisms and/or melanized microorganisms will be used for coating surfaces. As an example, melanin in increasing amounts starting from 1 g will be suspended in 30 mL of water. Drops of this concentrated melanin suspension will be allowed to spread on the hydrophilized surface of a plastic or glass. The water will be allowed to evaporate leaving melanin attached to the surface of the plastic or glass. As an alternative, a melanin coating may be made on surfaces by first immobilizing on the surface the enzyme laccase which catalyzes melanin formation in fungi. Melanin coated surfaces may also be generated by autopolymerization of melanin precursors. Enzymatically-mediated generation of melanin in situ could provide an attractive alternative for coating vulnerable surfaces with this material. Since melanin nanoshells are negatively charged, they can be attracted or held in place with positively charged substances, or repelled using negatively charged substances.

Protection of subjects against radiation: Melanin isolated from melanized organisms and/or melanized microorganisms will be used for protection against radiation. As an example, a sterile preparation of melanin, such a melanin nanospheres, will be injected into an individual at risk for radiation injury. The melanin nanospheres localize to the bone marrow where they provide shielding against the cytotoxic effects of radiation on vulnerable cells. In another application an oral preparation of melanin particles will be ingested to provide protection for the gastrointestinal mucosa. Melanin and melanized microorganisms can also be used in protective clothing and gear.

Containment of metal ions: Melanin isolated from melanized organisms and/or melanized microorganisms will be used for containment of metal ions. Since melanin nanoshells are negatively charged, they may be used to contain positively charged compounds, for example to act as metal chelators and to contain mercury.

Absorption of radiation: Melanin isolated from melanized organisms and/or melanized microorganisms will be used for absorption of radiation. For example, melanin may be used to absorb radiation, for example to absorb radar or energy generated in association with NMR systems.

Industrial, physical buildings and construction: Melanin isolated from melanized organisms and/or melanized microorganisms will be used. Melanin and melanized microorganisms may be used for shielding or containment in buildings, construction and containment structures in connection with, for example, concrete, plastics, steel, titanium, composites, coatings, "wafer" boards or sheeting in walls, roofs, flooring, and conduits. Melanin and melanized microorganisms may be used, for example, in shielding in connection with industrial radiation shielding; X-Ray rooms and enclosures x-rays, gamma radiation); storage and process equipment; airport detection systems (gamma radiation); hot cells (gamma radiation); paints and pigments (alpha and beta particles); glass (alpha particles/radon); power lines (EM radiation/EM field); conductors (EM radiation/EM field); wiring (EM radiation/EM field), transformers (EM radiation/EM field); switches (EM radiation/EM field); meter boxes (EM radiation/EM field); line hardware (EM radiation/EM field); fuses (EM radiation/EM field); breakers (EM radiation/EM field); drywall (alpha particles/radon); plywood (alpha particles/radon); doors (alpha particles/radon); door frames (alpha particles/radon), window frames (alpha particles/radon); granite (alpha particles/radon); concrete (alpha particles/radon); ceramic materials (tile); commercial fertilizers (alpha particles/radium); angles (alpha particles/radon); pigs (alpha particles/radon); castings alpha particles/radon); heat lamps (infrared radiation, UV light); road construction materials; pipes and colts (alpha particles/radon); heaters (infrared radiation); radio wave transmitters (EM radiation/radio waves); industrial Radiographers (x-ray and gamma radiation); roof tiles (alpha particles/radon); metal (alpha particles/radon); steel (alpha particles/radon); titanium (alpha particles/radon); stucco (alpha particles/radon); caulk (alpha particles/radon); plastic (all types of radiation); mortar (alpha particles/radon); brick (alpha particles/radon); and VDUs (Vacuum Distillation units) (all types of radiation). This includes the use of melanin and melanized microorganisms in fossil-fuel power plants, chemical plants, paper plants, etc. and clean-up/binding of mercury and other toxic release inventory (TRI) gases/metals emissions.

Operational Equipment: Melanin isolated from melanized organisms and/or melanized microorganisms will be used. Melanin and melanized microorganisms may be used for shielding and containment in composites, coatings, or inserts in all equipment with radiation exposure; for pressurized water reactors (PWRs), equipment on primary sides of plant, including, but not limited to, reactor core, reactor vessel, steam generators, pumps, conduit, electrical relay boxes; in boiling water reactors (BWRs), primary side equipment including boilers, pumps, conduits, and also secondary side equipment including turbines, condensers, pumps, relays, and generators where radiation exists.

Airlines: Melanin isolated from melanized organisms and/or melanized microorganisms will be used. Melanin may be used, for example, in shielding in air craft in connection with, for example, airplane materials (windows, cockpit gauges, mechanical parts, etc.) (cosmic radiation); cabinet X-ray system x-rays); human X-ray scanner x-rays); and blimps (cosmic radiation).

Space: Melanin isolated from melanized organisms and/or melanized microorganisms will be used. Melanin and melanized microorganisms may be used for shielding and containment in air craft in connection with, for example, astronaut jumpsuits (galactic cosmic radiation), spacecraft parts (galactic cosmic radiation), and rocket parts (engines, turbines, etc.) (galactic cosmic radiation).

Vehicles: Melanin isolated from melanized organisms and/or melanized microorganisms will be used. Melanin and melanized microorganisms may be used for shielding and containment in connection with, for example, ship parts (hull, engines, motor, etc.), vehicle parts, gauges (beta particles/tritium), and alternate fuel sources (e.g. nuclear energy).

Defense Application: Melanin isolated from melanized organisms and/or melanized microorganisms will be used. Melanin and melanized microorganisms may be used for shielding and containment in defense applications in connection with, for example, helicopter materials (cosmic radiation); submarine materials (alpha particles, beta particles, x-rays, and gamma radiation); navy carrier parts (alpha particles, beta particles, x-rays, and gamma radiation); fighter jet parts (cosmic radiation); tank parts (alpha particles, beta particles, x-rays, and gamma radiation); naval nuclear propulsion (alpha particles, beta particles, x-rays, and gamma radiation); nuclear powered vehicles; and weapon night sights (e.g., night vision goggles) (beta particles/tritium; infrared radiation). Other applications include use of melanin and melanized microorganisms in radar elusion in manned and unmanned vehicles.

Nuclear Application: Melanin isolated from melanized organisms and/or melanized microorganisms will be used. Radioactive materials in nuclear applications give off the following types of radiation: alpha particles, beta particles, x-rays, gamma rays, protons, neutrons and heavy ions. Melanin and melanized microorganisms may be used for shielding and containment in nuclear applications in connection with, for example, power plant building materials, decay drums, waste containers, power reactors, pressurized water reactors, plant building materials, reactor core, reactor vessel, steam generators, steam turbines, pumps, electrical relay boxes, conduits, boiling water reactors, boilers, pumps, condensers, relays, respirators, neutron generators, nuclear fuel reprocessors, master-slave manipulators, nuclear batteries, radiation fallout material, and tools, gear, and equipment. In radioactive material or waste storage, including spent fuel storage, melanin and melanized microorganisms may be used for shielding and containment in building material, equipment, and fuel cladding. In transport of radioactive material or waste, melanin and melanized microorganisms may be used for shielding and containment in packaging, containers, trucks/railcars/planes/water vessels, and covering/coating/composites. In radiation contamination clean-up, melanin and melanized microorganisms may be used for stabilizing radioactive isotopes in clean-up conditions.

Homeland security: Melanin isolated from melanized organisms and/or melanized microorganisms will be used. Melanin and melanized microorganisms may be used for shielding and containment in homeland security applications in connection with, for example, protection of buildings, equipment, computers, satellites, etc. and protection of masses of people through clothing applications, house shielding, etc. from nuclear or "dirty" bombs.

Medical/dental. Melanin isolated from melanized organisms and/or melanized microorganisms will be used. Melanin and melanized microorganisms may be used for shielding and containment in medical and dental applications in connection with, for example, MRI machines (gamma radiation); X-Ray machines (gamma radiation); mammogram machines (gamma radiation); lasers (infrared radiation); dental crowns (gamma radiation/uranium); PET Scans (beta particles); dental porcelains (gamma radiation/uranium/thorium); external-beam radiation therapy machines (used to target localized areas of a tumor) (gamma radiation, electron beams, neutron and heavy ion beams); X-ray Tubes (gamma radiation); lab coats, coveralls, and head covers; sterilizers (gamma radiation/cobalt-60); sonogram machines (gamma radiation); radiopharmaceuticals (injectable radioisotopes) (gamma, alpha, beta (both positive and negative) and Auger electron radiation); medical diagnostic imaging; cardiac cath swing lab shielded partitions (gamma radiation); and nuclear medicine products (gamma, alpha, beta (both positive and negative) and Auger electron radiation). In medical radiation therapy, melanin may be used in coatings to protect, for example, the following against x-ray and gamma radiation: linear accelerator swinging door systems, linear accelerator sliding door systems, H.D.R. automated swing door systems, gamma knife door systems, H.V.A.C. shielding systems, H.D.R. treatment enclosures, treatment room shielding upgrade systems, square-edge and interlocking bricks, modular vault systems, and proton therapy shielding systems.

Science Labs: Melanin isolated from melanized organisms and/or melanized microorganisms will be used. Melanin and melanized microorganisms may be used in shielding in science laboratories in connection with, for example, anodes x-rays), atomic particle accelerators x-rays, UV radiation), X-Ray diffraction units x-rays), and electron microscopes (EM radiation, x-rays, and beta particles).

Consumer products: Melanin isolated from melanized organisms and/or melanized microorganisms will be used. Melanin may be used, for example, in shielding in consumer products in connection with, for example, protective clothes, shoes, sunglasses (EM radiation/UV light), eye glasses (EM radiation/UV light), contacts (EM radiation/UV light), make-up (EM radiationlUV light), lip gloss (EM radiation/UV light), ovens (alpha particles), toaster ovens (alpha particles), cell phone and covers (EM radiation/radio waves); televisions (alpha particles, extremely low frequency EM fields, x-rays), watches (beta particles/tritium), glow in the dark products (beta particles), light bulbs (UV radiation, infrared radiation), fire alarms (alpha particles), smoke detectors (alpha particles/ americium-241; low energy gamma radiation), emergency exit signs (beta particles, tritium), tobacco (alpha particles), wireless technology, water fountains (alpha particles, radon), lantern mantles (alpha, beta, and gamma particles), lamp starters (beta particles, tritium, prometium; gamma particles, thorium), static eliminators (alpha particles/polonium-210), compasses (beta particles), batteries (beta particles/tritium); pagers (EM radiation), generators, purses, hats, gloves, shampoo and conditioner (EM radiation/UV light), hair spray (EM radiation/UV light), CRT (cathode-ray tube) monitors (x-rays), tanning bed goggles (EM radiation/UV light), cable tv wires (EM radiation), hair dryers (infrared radiation), pottery glaze (alpha, beta, and gamma particles), and food packaging materials.

Energy production, transmission and distribution: Melanin isolated from melanized organisms and/or melanized microorganisms will be used. Melanin and melanized microorganisms may be used in connection with, for example, coating/composites on conductors and wiring to reduce/avoid EdM radiation and line current losses, and coating/composites/inserts into electrical equipment and electrical working tools including, but not limited to, transformers (all sizes and types), switches, meter boxes, line hardware, fuses, and breakers, etc.

REFERENCES

1. Hill H Z (1992) The function of melanin or six blind people examine an elephant. Bioessays 14:49-56.
2. Jacobson E S (2000) Pathogenic roles for fungal melanins. Clin. Microbiol. Rev. 13:708-717.
3. Steenbergen J N, Shuman H A, Casadevall A (2001) *Cryptococcus neoformans* interactions with amoebae suggest an explanation for its virulence and intracellular pathogenic strategy in macrophages. Proc. Natl. Acad. Sci. USA. 98:15245-15250.
4. Nosanchuk J D, Casadevall A (2003) The contribution of melanin to microbial pathogenesis. Cell. Microbiol. 5: 203-223.
5. Robinson C H (2001) Cold adaptation in Arctic and Antarctic fungi. New phytologist 151: 341-353.
6. Wember V V, Zhdanova N N (2001) Peculiarities of linear growth of the melanin-containing fungi *Cladosporium sphaerospermum* Penz. and *Alternaria alternata* (Fr.) Keissler. Mikrobiol. Z. 63: 3-12.
7. Zhdanova N N, Tugay T, Dighton J, Zheltonozhsky V, McDermott P (2004) Ionizing radiation attracts soil fungi. Mycol Res. 108:1089-1096.
8. Mirchink T G, Kashkina G B, Abaturov I D (1972) Resistance of fungi with different pigments to radiation. Mikrobiologiia 41:83-86.
9. Saleh Y G, Mayo M S, Ahearn D G (1988) Resistance of some common fungi to gamma irradiation. Appl. Environm. Microbiol. 54:2134-2135.
10. Nicolaus R A (1968) Melanins. Hermann, Paris.
11. Wang Y, Aisen P. and Casadevall A (1996) Melanin, melanin "ghosts," and melanin composition in *Cryptococcus neoformans*. Infec. Immun. 64:2420-2424.
12. Eisenman H C, Nosanchuk J D, Webber J B, Emerson R J, Carnesano T A et al (2005) Microstructure of cell wall-associated melanin in the human pathogenic fiingus *Cryptococcus neoformans*. Biochemistry 44:3683-3693.
13. Dadachova E, Howell R W, Bryan R A, Frenkel A, Nosanchuk J D et al (2004) Susceptibility of the human pathogenic fungi *Cryptococcus neoformans* and *Histoplasma capsulatum* to gamma-radiation versus radioimmunotherapy with alpha- and beta-emitting radioisotopes. J. Nucl. Med. 45:313-320.
14. Sorenson J A, Phelps M E (1987) Physics in Nuclear Medicine. WB Saunders Company, Philadelphia.
15. Starratt A N, Ross L M, Lazarovits G (2002) 1,8-Dihydroxynaphthalene monoglucoside, a new metabolite of *Sclerotinia sclerotiorum*, and the effect of tricyclazole on its production. Can. J. Microbiol. 48:320-325.
16. Feng, B., Wang, X., Hauser, M., Kaufmann, S., Jentsch, S., Haase, G., Becker, J. M. and Szaniszlo, P. J. (2001) Molecular cloning and characterization of WdPKS1, a gene involved in dihydroxynaphthalene melanin biosynthesis and virulence in *Wangiella* (*Exophiala*) *dermatitidis*. Infect Immun 69, 1781-1794.
17. Croute F, Soleilhavoup J P, Vidal S, Dupouy D, Planel H. (1982) Paramecium tetraurelia growth simulation under low-level chronic irradiation. Investigations of a possible mechanism. Rad. Res. 92:560-567.
18. Conter A, Dupouy D, Delteil C, Planel H. (1986) Influence of very low doses of ionizing radiation on *Synechoccus lividus* metabolism during the initial growth phase. Arch Microbiol. 144:286-290.
19. Wilczok T, Bilinska B, Buszman E, Kopera M (1984) Spectroscopic studies of chemically modified synthetic melanins. Arch. Biochem. Biophys. 231:257-262.

20. Ito S. Fujita K (1985) Microanalysis of eumelanin and pheomelanin in hair and melanomas by chemical degradation and liquid chromatography. Anal. Biochem. 144:527-536.
21. Wakarmatsu K, Ito S (2002) Advanced chemical methods in melanin determination. Pigment Cell Res. 15:174-183.
22. Garcia-Rivera J, Eisenman H C, Nosanchuk J D, Aisen P, Zaragoza 0, Moadel T, Dadachova E, Casadevall A. (2005) Comparative analysis of *Cryptococcus neoformans* acid-resistant particles generated from pigmented cells grown in different laccase substrates. Fungal Genet Biol. 42:989-998.
23. Frases S, Chaskes S, Dadachova E, Casadevall A. (2006) Induction by *Klebsiella* aerogenes of a melanin-like pigment in *Cryptococcus neoformans*. Appl Environ Microbiol. 72:1542-1550.
24. Hall E J (2000) Radiobiology for the Radiologist. Lippincott Williams & Willkins, Philadelphia, p. 91-94.
25. Enochs W S, Nilges M J, and Swartz H M (1993) A standardized test for the identification and characterization of melanins using electron paramagnetic resonance (EPR) spectroscopy. Pigment Cell Res. 6:91-99.
26. Bhandari R (1985) Scattering coefficients for a multilayered sphere: analytic expressions and algorithms. App. Opt. 24:1960-1974.
27. Forest S E, Lam W C, Millar D P, Nofsinger J B, and Simon J D (2000) A Model for the Activated Energy Transfer within Eumelanin Aggregates. J. Phys. Chem. B 104: 811-814.
28. Gan E V, Haberman H F, Menon I A (1976) Electron transfer properties of melanin. Arch. Biochem. Biophys. 173: 666-672.
29. Hulot G, Gallet Y (2003) Do superchrons occur without any palaeomagnetic warning? Earth Planetary Sci. Lett 210:191-201.
30. Davis M, Hut P and Muller R A (1985) Terrestrial catastrophism: Nemesis or Galaxy? Nature 313:503.
31. Casadevall A (2005) Fungal virulence, vertebrate endothermy, and dinosaur extinction: is there a connection? Fungal Genet. Biol. 42:98-106.
32. Beatty J T, Overmann J, Lince M T, Manske A K, Lang A S et al (2005) An obligately photosynthetic bacterial anaerobe from a deep-sea hydrothermal vent. Proc. Nat. Acad. Sci. USA 102:9306-9310.
33. http://www.sbs.utexas.edu/mycology/sza_protocols_media.htm
34. dellaCioppa G, Garger S J, Sverlow G G, Turpen T H, Grill L K. (1990) Melanin production in *Escherichia coli* from a cloned tyrosinase gene. Biotechnology (NY) 8(7): 634-8.
35. Sambrook J, Fritsch E F, Maniatis T. Molecular Cloning. A Laboratory Manuel, Second edition. Cold Spring Harbor Laboratory Press, 1989.
36. Salas S D, J E Bennett, K J Kwon-Chung, J R Perfect, and P R Williamson (1996) Effect of the laccase gene CNLAC1, on virulence of *Cryptococcus neoformans*. J. Exp. Med. 184: 377-386.
37. Moriwaki A, Kihara J, Kobayashi T, Tokunaga T, Arase S, Honda Y. Insertional mutagenesis and characterization of a polyketide synthase gene (PKS1) required for melanin biosynthesis in *Bipolaris oryzae*. FEMS Microbiol Lett. 2004 238(1):1-8.
38. Kihara J, Moriwaki A, Ueno M, Tokunaga T, Arase S, Honda Y. Cloning, functional analysis and expression of a scytalone dehydratase gene (SCD1) involved in melanin biosynthesis of the phytopathogenic fungus *Bipolaris oryzae*. Curr Genet. 2004 45(4):197-204. Epub 2004 Jan. 10.
39. Loppnau P, Tanguay P, Breuil C. Isolation and disruption of the melanin pathway polyketide synthase gene of the softwood deep stain fungus *Ceratocystis resinifera*. Fungal Genet Biol. 2004 January; 41(1):3341.
40. Shimizu K, Tanaka C, Peng Y L, Tsuda M. Phylogeny of *Bipolaris* inferred from nucleotide sequences of Brn1, a reductase gene involved in melanin biosynthesis. J Gen Appl Microbiol. 1998 August; 44(4):251-258.
41. Wang H L, Kim S H, Breuil C. A scytalone dehydratase gene from *Ophiostoma floccosum* restores the melanization and pathogenicity phenotypes of a melanin-deficient *Colletotrichum lagenarium* mutant. Mol Genet Genomics. 2001 September; 266(1):126-32.
42. Kubo Y, Takano Y, Endo N, Yasuda N, Tajima S, Furusawa I. Cloning and structural analysis of the melanin biosynthesis gene SCD1 encoding scytalone dehydratase in *Colletotrichum lagenarium*. Appl Environ Microbiol. 1996 December; 62(12):4340-4.
43. Mercado-Blanco J. Garcia F, Fernandez-Lopez M, Olivares J. Melanin production by *Rhizobium meliloti* GR4 is linked to nonsymbiotic plasmid pRmeGR4b: cloning, sequencing, and expression of the tyrosinase gene mepA. J. Bacteriol. 1993 September; 175(17):5403-10.
44. Urabe K, Aroca P, Hearing V J. From gene to protein: determination of melanin synthesis. Pigment Cell Res. 1993 August; 6(4 Pt 1):186-92.
45. Fuqua W C, Weiner R M. The melA gene is essential for melanin biosynthesis in the marine bacterium *Shewanella colwelliana*. J Gen Microbiol. 1993 May; 139(5):1105-14.
46. Bonner, T. G., A. Duncan. 1962. Infra-red spectra of some melanins. *Nature* 194:1078-1079.
47. Chaskes, S, and R. L. Tyndall. 1975. Pigment production by *Cryptococcus neoformans* from para- and ortho-diphenols: effect of the nitrogen source. *J. Clin. Microbiol.* 1:509-514.
48. Chaskes, S, and R. L. Tyndall. 1978. Pigment production by *Cryptococcus neoformans* and other *Cryptococcus* species from aminophenols and diaminobenzenes. *J. Clin. Microbiol.* 7:146-152.
49. Chaskes, S, and R. Tyndall. 1978. Pigmentation and autoflourescence of *cryptococcus* species after growth on tryptophan and anthranilic acid media. *Mycopathologia* 64:105-112.
50. Longuet-Higgins, H. C. 1960. On the origin of the free radical property of melanins. *Archives of Biochemistry and Biophysics* 86:231-232.
51. Mason, H. S., D. J. E. Ingram, and B. Allen. 1960. The free radical property of melanins. *Archives of Biochemistry and Biophysics* 86:225-230.
52. Kuhn D M, Balkis M, Chandra J, Mukherjee P K, Ghannoum M A. (2003). Uses and limitations of the XTT assay in studies of *Candida* growth and metabolism. *J Clin Microbiol.* 41: 506-8.
53. Berridge M V, Herst P M, Tan A S. (2005) Tetrazolium dyes as tools in cell biology: new insights into their cellular reduction. *Biotechnol Annu Rev.* 11: 127-52.
54. Hicks J K, D'Souza C A, Cox G M, Heitman J. (2004) Cyclic AMP-dependent protein kinase catalytic subunits have divergent roles in virulence factor production in two varieties of the fungal pathogen *Cryptococcus neoformans*. Eukaryot Cell 3:14-26.
55. Boomer S M, Pierson B K, Austinhirst R, Castenholz R W. (2000) Characterization of novel bacteriochlorophyll-a- containing red filaments from alkaline hot springs in Yellowstone National Park. Arch Microbiol. 174:152-161.

What is claimed is:

1. A method of enhancing growth of a microorganism comprising increasing melanin content in the microorganism in an amount effective to enhance growth of the microorganism when the microorganism is exposed to ionizing radiation in a condition of limited nutrient supply for the microorganism, and exposing the microorganism in which melanin content has been increased to ionizing radiation in a condition of limited nutrient supply for the microorganism to thereby enhance the growth of the microorganism in which melanin content has been increased compared to growth of the microorganism in which melanin content has not been increased.

2. The method of claim 1, wherein melanin content in the microorganism is increased by a method comprising growing the microorganism in the presence of a melanin precursor.

3. The method of claim 2, wherein the melanin precursor is one or more of L-dopa (3,4-dihydroxyphenylalanin), D-dopa, catechol, 5-hydroxyindole, tyramine, dopamine, tyrosine, cysteine, m-aminophenol, o-aminophenol, p-aminophenol, 4-aminocatechol, 2-hydroxyl-1,4-naphthaquinone, 4-metholcatechol, 3,4-dihydroxynaphthalene, gallic acid, resorcinol, 2-chloroaniline, p-chloroanisole, 2-amino-p-cresol, 4,5-dihydroxynaphthalene, 1,8-dihydroxynaphthalene, 2,7-disulfonic acid, o-cresol, m-cresol, and p-cresol.

4. The method of claim 1, wherein the melanin content in the microorganism is increased by a method comprising transforming the microorganism with one or more genes involved in melanin biosynthesis.

5. The method of claim 1, wherein the microorganism is a fungus or a bacterium.

6. The method of claim 5, wherein the fungus is *Cryptococcus neoformans* or *Histoplasma capsulatum* or *Wangiella dermatitidis*.

7. The method of claim 1, wherein the melanin comprises one or more of allomelanin, pheomelanin and eumelanin.

8. The method of claim 1, wherein the microorganism is exposed to ionizing radiation in a condition of limited glucose supply for the microorganism.

9. The method of claim 1, wherein the microorganism is exposed to ionizing radiation at a dose that is sublethal for a non-melanized microorganism.

* * * * *